US007754422B2

(12) United States Patent
Tanaka et al.

(10) Patent No.: US 7,754,422 B2
(45) Date of Patent: Jul. 13, 2010

(54) METHOD OF JUDGING INFLAMMATORY DISEASE

(75) Inventors: Toshihiro Tanaka, Tokyo (JP); Yozo Ohnishi, Tokyo (JP); Koichi Ozaki, Tokyo (JP); Aritoshi Iida, Kanagawa (JP); Yusuke Nakamura, Kanagawa (JP); Masatsugu Hori, Suita (JP)

(73) Assignee: Riken, Saitama (JP)

( * ) Notice: Subject to any disclaimer, the term of this patent is extended or adjusted under 35 U.S.C. 154(b) by 339 days.

(21) Appl. No.: 10/523,723

(22) PCT Filed: Aug. 8, 2003

(86) PCT No.: PCT/JP03/10131

§ 371 (c)(1),
(2), (4) Date: Nov. 29, 2005

(87) PCT Pub. No.: WO2004/015100

PCT Pub. Date: Feb. 19, 2004

(65) Prior Publication Data

US 2006/0147920 A1 Jul. 6, 2006

(30) Foreign Application Priority Data

Aug. 8, 2002 (JP) .............................. 2002-231532

(51) Int. Cl.
*C12Q 1/68* (2006.01)
(52) U.S. Cl. ......................................................... 435/6
(58) Field of Classification Search ....................... None
See application file for complete search history.

(56) References Cited

U.S. PATENT DOCUMENTS

2007/0190528 A1  8/2007  Tanaka et al.

FOREIGN PATENT DOCUMENTS

| JP | 2002-136291 | 5/2002 |
| WO | 98/47004 | 10/1998 |
| WO | 00/58522 | 10/2000 |
| WO | 03/034896 | 5/2003 |

OTHER PUBLICATIONS

GenBank Accession No. AF129756 (Oct. 28, 1999) NCBI website.*
Ozaki et al. (Nature genetics 2002 vol. 32 p. 650).*
Witte et al. (European Journal of Human Genetics 2002 vol. 10 p. 82).*
Trabetti et al. Jouranl Med Geenet 1999 vol. 36 p. 323.*
Newton-Cheh et al. 2004 JAMA vol. 291 p. 3008.*
Tobin et al. (European Heart Journal 2004 vol. 25 p. 459).*
Asselbergs et al. (Clinical Science 2007 vol. 112 p. 291).*
Definition of Arterioscelerosis www.medterms.com.*
types of atherosclerosis http://www.wrongdiagnosis.com/a/atherosclerosis/subtypes.*

Breslow, "Cardiovascular disease burden increases, NIH funding decreases," Nature Medicine, vol. 3, No. 6, pp. 600-601 (1997).
Braunwald, "Shattuck Lecture—Cardiovascular Medicine at the turn of the millennium: Triumphs, concerns, and opportunities," The New England Journal of Medicine, vol. 377, pp. 1360-1369 (1997).
Risch et al., "The Future of Genetic Studies of Complex Human Diseases," Science, vol. 273, pp. 1516-1517(1996).
Collins et al., "Variations on a Theme: Cataloging Human DNA Sequence Variation," Science, vol. 278, pp. 1580-1581 (1997).
Lander, "The New Genomics: Global Views of Biology," Science, vol. 174, pp. 536-539 (1996).
Ross, "Atherosclerosis—An Inflammatory Disease," The New England Journal of Medicine, vol. 340, No. 2, pp. 115-126 (1999).
Ozaki et al., "Functional SNPs in the lymphotoxin-α gene that are associated with susceptibility to myocardial infarction," Nature Genetics, vol. 32, pp. 650-654 (2002).
Iida et al., "Catalog of 258 single-nucleotide polymorphisms (SNPs) in genes encoding three organic anion transporters, three organic anion-transporting polypeptides, and three NADH: ubiquinone oxidoreductase flavoproteins," Journal of Human Genetics, vol. 46, pp. 668-683 (2001).
Ohnishi et al., "A high-throughput SNP gypping system for genome-wide association studies," Journal of Human Genetics, vol. 46, pp. 471-477 (2001).
Yamada et al., "Association between a Single-Nucleotide Polymorphism in the Promoter of the Human Interleukin-3 Gene and Rheumatoid Arthritis in Japanese Patients, and Maximum-Likelihood Estimation of Combinatorial Effect That Two Genetic Loci Have on Susceptibility to the Disease," American Journal of Human Genetics, vol. 68, pp. 674-685 (2001).
Albertella et al., "Characterization of a novel gene in the human major histocompatibility complex that encodes a potential new member of the I kappa B gamily of proteins," Human Molecular Genetic, vol. 3, No. 5, pp. 793-799 (1994).
Messer et al., "Polymorphic Structure of the Tumor Necrosis Factor (TNF) Locus: An NcoI Polymorphism in the First Intron of the Human TNF-62 Gene Correlates with A Variant Amino Acid on Position 26 and a Reduced Level of TNF-β Production," The Journal of Experimental Medicine, vol. 173, pp. 209-219 (1991).
Andrews et al., "A rapid micropreparation technique for extraction of DNA-binding proteins from limiting numbers of mammalian cells," Nucleic Acids Research, vol. 19, No. 9, p. 2499 (1991).

(Continued)

*Primary Examiner*—Sarae Bausch
*Assistant Examiner*—Katherine Salmon
(74) *Attorney, Agent, or Firm*—Greenblum & Bernstein, P.L.C.

(57) ABSTRACT

The object of the present invention is to determine inflammatory diseases such as myocardial infarction by identifying single nucleotide polymorphisms (SNPs) associated with myocardial infarction and utilizing these SNPs. The present invention provides a method for determining an inflammatory disease, which comprises detecting at least one gene polymorphism existing in at least one gene selected from the group consisting of a lymphotoxin-α (LT-α) gene, an I Kappa B-like (IKBL) gene, and a BAT1 gene; an oligonucleotide used in said method; a kit for diagnosing an inflammatory disease which comprises said oligonucleotide; and use thereof. The present invention further provides a method for treating an inflammatory disease; and a method for screening for a therapeutic agent for an inflammatory disease.

4 Claims, 6 Drawing Sheets

OTHER PUBLICATIONS

Ware et al., "The Ligans and Receptors of the Lymphotoxin System," Current Topics in Microbiology and Immunology, vol. 198, pp. 175-218 (1995).

English Language Abstract of JP 2002-136291.

U.S. Appl. No. 11/813,450, filed Jul. 6, 2007, entitled "Method of Judging Inflammatory Disease by Using Single Nucleotide Polymorphism."

Office Action for Japanese Patent Application No. 2004-527375.

Padovani et al., Thrombosis Research, (2000), vol, 100, pp. 263-269.

Park et al., Hypertension Research, (2002), vol, 25, No. 3, pp. 389-394.

English Translation of the relevant portion of the Office Action for Japanese Patent Application No. 2004-527375.

Keso et al,, "Polymorphisms within the tumor necrosis factor locus and prevalence of coronary artery disease in middle-aged men," Atherosclerosis, vol. 154, No. 3, pp. 691-697 (2001).

Koch et al., "Interleukin-10 and tumor necrosis factor gene polymorphisms and risk of coronary artery diseases and myocardial infarction," Atherosclerosis, vol. 159, No. 1, pp. 137-144 (2001).

Pandey et al., "TNF-$\alpha$ and TNF-$\beta$ Gene Polymorphisms in Systemic Sclerosis," Human Immunology, vol. 60, pp. 1128-1130 (1999).

English translation of the International Preliminary Examination Report of PCT/JP2003/010131, dated Jan. 25, 2005.

* cited by examiner

A

B

A

B

METHOD OF JUDGING INFLAMMATORY DISEASE

TECHNICAL FIELD

The present invention relates to a method for determining inflammatory diseases, which comprises detecting gene polymorphisms existing in an LT-α gene and the like, an oligonucleotide to be used in the method, a kit for diagnosing inflammatory diseases comprising the oligonucleotide, and the use thereof. Furthermore, the present invention also relates to a method for treating inflammatory diseases using LT-α and a method for screening for therapeutic agents for inflammatory diseases using LT-α.

BACKGROUND ART

Despite changes in lifestyle and new pharmacologic approaches, coronary artery diseases including myocardial infarction continue to be the principal cause of death in many countries (Breslow, J. L., Nature Med. 3, 600-601, 1997; Braunwald, E., N. Engl. J. Med., 337, 1360-1369, 1997). Accordingly, the identification of genetic and environmental factors in the onset of these diseases is highly anticipated.

Common genetic variants are known to be significantly associated with risks of contacting lifestyle-related diseases such as diabetes mellitus and hypertension (Risch, N., et al., Science, 273, 1516-1517, 1996; Collins, F. S., et al., Science, 278, 1580-1581, 1997; Lander, E. S., et al., Science, 274, 536-539, 1996). To identify genes susceptible to polygenic diseases, a method utilizing "linkage" and a method utilizing "association" are known. Linkage-based analysis involves detecting whether the locus of a gene susceptible to a disease and the locus of a gene marker (mainly microsatellite) are linked; that is, examining the relationship between gene loci. In contrast, association-based analysis involves detecting which type (allele) of specific gene markers (mainly single nucleotide polymorphisms: SNPs) is associated with a disease; that is, examining the relationship between alleles. Hence, it can be said that association-based analysis using common variants as markers is far more powerful than linkage-based analysis utilizing localization of genes related to such diseases. Single nucleotide polymorphisms (SNPs) can be useful polymorphism markers when genes associated with vulnerability to diseases or drug reactivity are searched for. SNPs may directly affect gene products quantitatively and qualitatively or may increase the risk of severe side effects due to diseases or drugs. Therefore, it is expected that the search for many SNPs can contribute to identification of disease-related genes and to the establishment of diagnostic methods whereby side effects of drugs can be avoided.

In a region of approximately 130 kb on human chromosome 6p21, there exist lymphotoxin-α (LT-α), tumor necrosis factor-α (TNF-α), LST1, 1C7, allograft inflammatory-factor-1 (AIF-1), I kappa B-like protein (IKBL), V-ATPase G-subunit like protein (ATP6G), BAT1, MICB, and p5-1. LT-α (also known as TNF-β) is one of the cytokines produced during the earliest phase of the process of angiitis and takes a homotrimeric structure wherein β sheet structures are piled up in the shape of sandwich. LT-α activates the cytokine cascade by inducing other mediators such as interleukin-1 and adhesion molecules (Ross, R., N. Engl. J. Med., 340, 115-126, 1999). Inflammatory mediators such as cytokines are known to be involved in atheroma formation and atheroma lesions so as to induce luminal thrombosis (Ross, R., N. Engl. J. Med., 340, 115-126, 1999). IKBL is located on 6p21.3 in major histocompatibility complex (MHC) class II region. It has been reported that IKBL resembles an inhibitor (IKB) family protein of a κ light chain gene in B cells. Proteins of the IKB family have action to inhibit a nuclear factor of a κ light chain gene enhancer within B cells.

For the relationship between gene mutation and myocardial infarction, a method for determining a genetic factor of myocardial infarction by analyzing polymorphisms of a human prostacyclin synthetase gene has been known (JP Patent Publication (Kokai) No. 2002-136291 A). However, the association between a gene mutation existing in the region of approximately 130 kb on the above 6p21 and myocardial infarction has not yet been reported.

SUMMARY OF THE INVENTION

The objects of the present invention are to provide a method for determining inflammatory diseases such as myocardial infarction which involving identifying gene polymorphisms associated with myocardial infarction and using the gene polymorphisms, an oligonucleotide that can be used for the method, a kit for diagnosing inflammatory diseases, a method for treating inflammatory diseases, and the like.

To achieve the above object, the present inventors have typed SNPs within human LT-α, IKBL, and BAT1 genes respectively for a group of about 1000 myocardial infarction patients and a control group of about 1000 person by a multiplex PCR-invader assay method, so that association-based analysis was performed by case-control study. As a result, it has been identified that the frequencies of these SNPs are statistically and significantly high in myocardial infarction patients. Furthermore, by the experiments using a luciferase assay method and recombinant proteins, a possibility has been found that these SNPs affect the transcriptional activities of the genes, thus changing the amounts of the resulting gene products, and such changes then induce diseases such as myocardial infarction. The present invention has been completed based on such findings.

Thus, according to the present invention, there is provided a method for determining an inflammatory disease, which comprises detecting at least one gene polymorphism existing in at least one gene selected from the group consisting of a lymphotoxin-α (LT-α) gene, an I Kappa B-like (IKBL) gene, and a BAT1 gene.

Specifically, according to the present invention, there is provided a method for determining an inflammatory disease, which comprises detecting at least one single nucleotide polymorphism existing in at least one gene selected from the group consisting of the lymphotoxin-α (LT-α) gene, the I Kappa B-like (IKBL) gene, and the BAT1 gene.

According to the present invention, there is further provided a method for determining an inflammatory disease, which comprises detecting at least one single nucleotide polymorphism selected from the group consisting of the following (1) to (5):

(1) a G/A polymorphism at nucleotide 10 in the nucleotide sequence of exon 1 of the LT-α gene shown in SEQ ID NO: 1;

(2) an A/G polymorphism at nucleotide 90 in the nucleotide sequence of intron 1 of the LT-α gene shown in SEQ ID NO: 2;

(3) a C/A polymorphism at nucleotide 80 in the nucleotide sequence of exon 3 of the LT-α gene shown in SEQ ID NO: 3;

(4) a T/A polymorphism at nucleotide 572 in the nucleotide sequence of a promoter of the IKBL gene shown in SEQ ID NO: 4; and (5) a G/C polymorphism at nucleotide 1228 in the nucleotide sequence of a promoter of the BAT1 gene shown in SEQ ID NO: 5.

According to the present invention, there is further provided a method for determining an inflammatory disease, which comprises detecting a gene polymorphism whereby an amino acid to be encoded is mutated from threonine to asparagine by substitution of at least one of the nucleotides 80 to 82 in the nucleotide sequence of exon 3 of the LT-α gene shown in SEQ ID NO: 3 with another nucleotide.

According to the present invention, there is further provided an oligonucleotide that can hybridize to a sequence of at least 10 continuous nucleotides containing at least one position selected from the group consisting of the following (1) to (5), the position being contained in the sequences shown in SEQ ID NOS: 1 to 5, or to a complementary sequence thereof, and is used as a probe in the above determination method:

(1) position 10 of the nucleotide sequence of exon 1 of the LT-α gene shown in SEQ ID NO: 1;
(2) position 90 of the nucleotide sequence of intron 1 of the LT-α gene shown in SEQ ID NO: 2;
(3) position 80 of the nucleotide sequence of exon 3 of the LT-α gene shown in SEQ ID NO: 3;
(4) position 572 of the nucleotide sequence of the promoter of the IKBL gene shown in SEQ ID NO: 4; and
(5) position 1228 of the nucleotide sequence of the promoter of the BAT1 gene shown in SEQ ID NO: 5.

According to the present invention, there is further provided an oligonucleotide that can amplify a sequence of at least 10 continuous nucleotides containing at least one position selected from the group consisting of the following (1) to (5), the position being contained in the sequences shown in SEQ ID NOS: 1 to 5, and/or to a complementary sequence thereof, and is used as a primer in the above determination method:

(1) position 10 of the nucleotide sequence of exon 1 of the LT-α gene shown in SEQ ID NO: 1;
(2) position 90 of the nucleotide sequence of intron 1 of the LT-α gene shown in SEQ ID NO: 2;
(3) position 80 of the nucleotide sequence of exon 3 of the LT-α gene shown in SEQ ID NO: 3;
(4) position 572 of the nucleotide sequence of the promoter of the IKBL gene shown in SEQ ID NO: 4; and
(5) position 1228 of the nucleotide sequence of the promoter of the BAT1 gene shown in SEQ ID NO: 5.

Furthermore, according to the present invention, there is provided a kit for diagnosing an inflammatory disease, which comprises 1 or more types of the above oligonucleotide.

According to another aspect of the present invention, there is provided a method for analyzing the expression state of LT-α, IKBL, or BAT1, which comprises detecting at least one single nucleotide polymorphism selected from the group consisting of the above (1) to (5).

According to a further aspect of the present invention, there is provided a method for measuring the transcriptional activity of LT-α, IKBL, or BAT1, which comprises introducing an LT-α, IKBL, or BAT1 gene fragment containing at least one single nucleotide polymorphism selected from the group consisting of the above (1) to (5) into a cell, culturing the cell, and analyzing the expression of the gene.

According to further another aspect of the present invention, there is provided a method for screening for a substance inhibiting the transcriptional activity of LT-α, IKBL, or BAT1, which comprises introducing an LT-α, IKBL, or BAT1 gene fragment containing at least one single nucleotide polymorphism selected from the group consisting of the above (1) to (5) into a cell, culturing the cell in the presence of a candidate substance inhibiting the transcriptional activity of LT-α, IKBL, or BAT1, and analyzing the expression of the gene.

According to a preferred embodiment of the present invention, there is provided any one of the above methods, which comprises introducing a transcriptional unit wherein a reporter gene is ligated downstream of the above LT-α, IKBL, or BAT1 gene fragment into a cell, culturing the cell, and analyzing the expression of the gene by measuring the reporter activity.

According to still another aspect of the present invention, there is provided a method for screening for a transcriptional regulatory factor of LT-α, which comprises bringing a gene fragment containing at least one single nucleotide polymorphism selected from the group consisting of the above (1) to (5) into contact with a sample wherein a transcriptional regulatory factor of LT-α, IKBL, or BAT1 is presumed to be present, and detecting binding of the above fragment with the transcriptional regulatory factor.

According to still another aspect of the present invention, there is provided a method for evaluating ability to induce an adhesion molecule in a cell, which comprises introducing a gene fragment containing a C/A polymorphism at nucleotide 90 in a nucleotide sequence of intron 1 of an LT-α gene shown in SEQ ID NO: 2 into a cell in which an adhesion molecule can be induced, and evaluating the ability to induce an adhesion molecule in the cell.

According to still another aspect of the present invention, there is provided a method for treating an inflammatory disease, which comprises suppressing the expression or activity of lymphotoxin-α (LT-α). Preferably, the inflammatory disease is myocardial infarction. In the above method, an antibody against lymphotoxin-α (LT-α) is preferably used.

According to still another aspect of the present invention, there is provided a therapeutic agent for an inflammatory disease, which comprises as an active ingredient a substance suppressing the expression or activity of lymphotoxin-α (LT-α). Preferably, the substance suppressing the expression or activity of lymphotoxin-α (LT-α) is an antibody against lymphotoxin-α.

According to still another aspect of the present invention, there is provided a method for screening for a therapeutic agent for an inflammatory disease, which comprises the steps of bringing a cell into contact with a candidate substance, analyzing the expression level of a gene encoding lymphotoxin-α (LT-α) within the cell, and selecting as a therapeutic agent for an inflammatory disease a candidate substance that lowers the expression level of the gene by comparison with a condition where the candidate substance is absent.

According to still another aspect of the present invention, there is provided a method for screening for a therapeutic agent for an inflammatory disease, which comprises the steps of bringing lymphotoxin-α (LT-α) into contact with a candidate substance, measuring the activity of lymphotoxin-α, and selecting as a therapeutic agent for an inflammatory disease a candidate substance that lowers the activity of lymphotoxin-α by comparison with a condition where the candidate substance is absent. Preferably, the activity of lymphotoxin-α is an activity to induce an adhesion molecule and/or a cytokine. Preferably, the adhesion molecule is VCAM-1, ICAM-1, or E-selectin, and the cytokine is TNF.

According to an example of the present invention, the expression level or activity of lymphotoxin-α (LT-α) is lowered through an increase in the expression level or activity of the IKBL gene.

BEST MODE FOR CARRYING OUT THE INVENTION

[1] Method for Determining Inflammatory Disease

Figure 1:
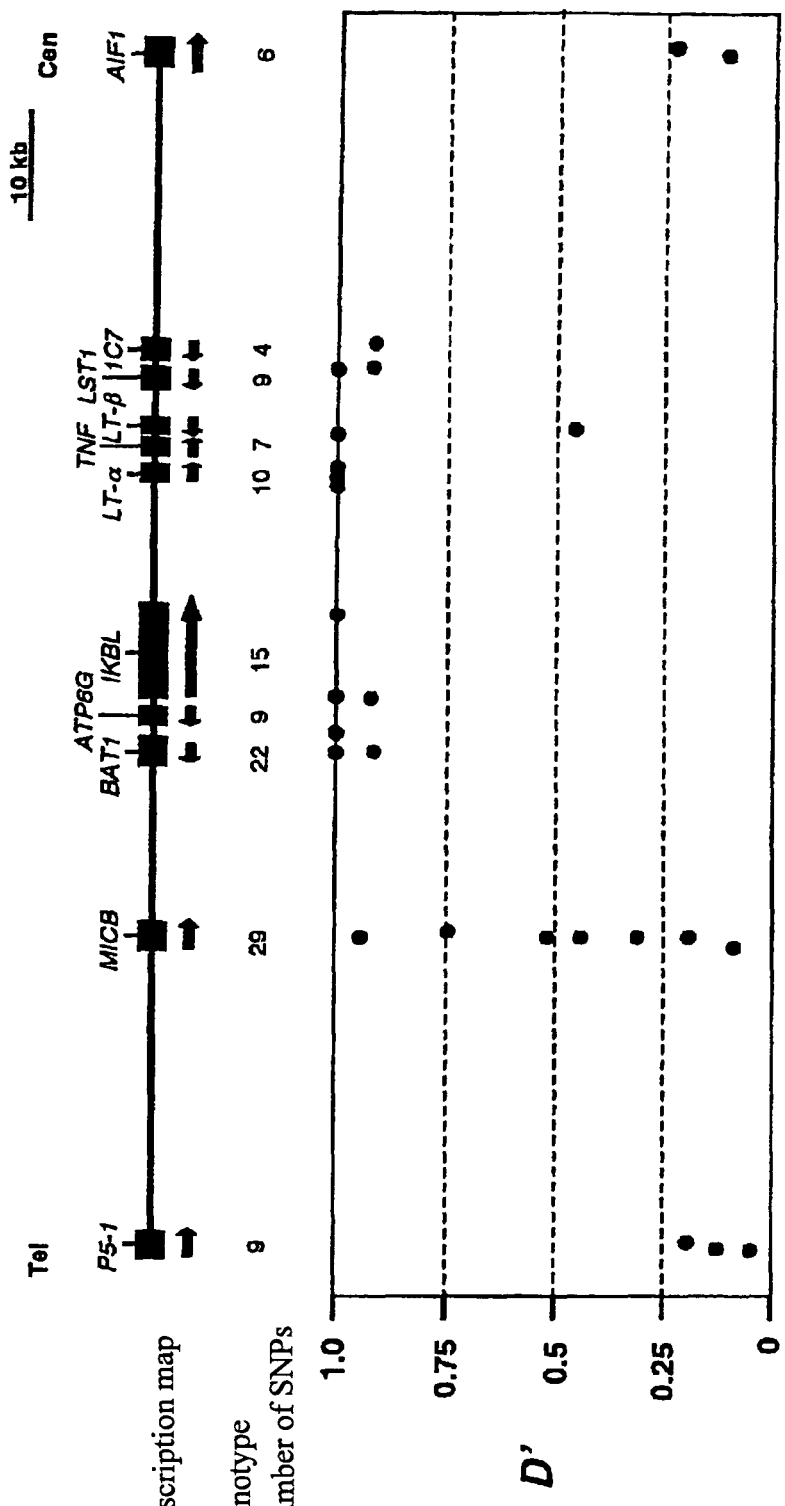
FIG. 1 shows linkage disequilibrium in the 130-kb genomic region containing the LT-α locus.
Upper: Transcription map indicating the number of genotyped SNPs in each gene.
Lower: Distribution of D' in this region. D' is shown for the SNP in intron 1 of LT-α versus other SNPs.

The method of the present invention is a method for determining the presence or absence of the onset of inflammatory diseases or the possibility of the onset of inflammatory diseases by detecting gene polymorphisms, particularly single nucleotide polymorphisms (SNPs), existing in specific genes showing association with inflammatory diseases.

The above-mentioned specific gene is at least one gene selected from the group consisting of a lymphotoxin-α (LT-α) gene (SEQ ID NO: 6), 1 Kappa B-like (IKBL) gene (SEQ ID NO: 7), and BAT1 gene (SEQ ID NO: 8), existing in a region of approximately 130 kb on human chromosome 6p21. The gene polymorphisms exist on exon, intron, and promoter regions of genomic DNA containing these genes.

In the present invention, "detecting gene polymorphisms (e.g., single nucleotide polymorphisms) existing in at least one gene selected from the group consisting of a lymphotoxin-α (LT-α) gene, an I Kappa B-like (IKBL) gene, and a BAT1 gene" means both (i) direct detection of the gene polymorphisms (referred to as polymorphisms on the gene side), and (ii) detection of polymorphisms (referred to as polymorphisms on the complementary side) existing on the complementary sequence side of the above gene so as to presume gene polymorphisms on the gene side from the detection result. However, since nucleotides on the gene side and nucleotides on the complementary sequence side are not always in a completely complementary relationship, it is preferable to directly detect polymorphisms on the gene side.

In addition, examples of polymorphisms on the complementary side to be detected in the present invention include gene polymorphisms that exist in at least one complementary sequence selected from the complementary sequence of the lymphotoxin- LT-α gene, that of the I Kappa B-like (IKBL) gene, and that of the BAT1 gene. More specific example is at least one single nucleotide polymorphism selected from the group consisting of the following (1) to (5):

(1) a C/T polymorphism in the complementary sequence of the LT-α gene and at a nucleotide complementary to nucleotide 10 in the nucleotcide sequence of exon 1 of the LT-α gene shown in SEQ ID NO: 1;

(2) a T/C polymorphism in the complementary sequence of the LT-α gene and at a nucleotide complementary to nucleotide 90 in the nucleotide sequence of intron 1 of the LT-α gene shown in SEQ ID NO: 2;

(3) a G/T polymorphism in the complementary sequence of the LT-α gene and at a nucleotide complementary to nucleotide 80 in the nucleotide sequence of exon 3 of the LT-α gene shown in SEQ ID NO: 3;

(4) an A/T polymorphism in the complementary sequence of the IKBL gene at a nucleotide complementary to nucleotide 572 in the nucleotide sequence of the promoter of the IKBL gene shown in SEQ ID NO: 4; and (5) a C/G polymorphism in the complementary sequence of the BAT1 gene at a nucleotide complementary to nucleotide 1228 in the nucleotide sequence of the promoter of the BAT1 gene shown in SEQ ID NO: 5.

In this specification, a nucleotide at position X ($X^{th}$ nucleotide) in a gene (e.g., LT-α gene) may be represented by a combination of X (number) representing the position and a symbol representing a nucleotide. For example, "10G" represents G at position 10 ($10^{th}$ position), "10A" indicates A at position 10, and "10G/A" represents G or A at position 10.

In this specification, nucleotide 90 of the nucleotide sequence of intron 1 of the LT-α gene shown in SEQ ID NO: 2 corresponds to nucleotide 252 (the $252^{nd}$ nucleotide) from the $1^{st}$ nucleotide of exon 1 of the LT-α gene. Furthermore, nucleotide 80 (the $80^{th}$ nucleotide) of the nucleotide sequence of exon 3 of the LT-α gene shown in SEQ ID NO: 3 corresponds to nucleotide 723 (the $723^{rd}$ nucleotide) when counted from the $1^{st}$ nucleotide of exon 1 of the LT-α gene.

Hence, in this specification, the G/A polymorphism at nucleotide 90 of the nucleotide sequence of intron 1 of the LT-α gene shown in SEQ ID NO: 2 may be represented by LT-α intron 1 252G/A, and the C/A polymorphism at nucleotide 80 of the nucleotide sequence of exon 3 of the LT-α gene shown in SEQ ID NO: 3 may be represented by LT-α exon 3 723C/A.

In this specification, nucleotide 572 of the nucleotide sequence of the promoter of the IKBL gene shown in SEQ ID NO: 4 corresponds to nucleotide 63 ($-63^{rd}$) from nucleotide 634 (supposed to be the $1^{st}$ nucleotide) in the downstream direction. Furthermore, nucleotide 1228 of the nucleotide sequence of the promoter of the BAT1 gene shown in SEQ ID NO: 5 corresponds to nucleotide 23 ($-23^{rd}$) from nucleotide 1250 (supposed to be the $1^{st}$ nucleotide) in the downstream direction.

Therefore, in this specification, the T/A polymorphism at nucleotide 572 of the nucleotide sequence of the promoter of the IKBL gene shown in SEQ ID NO: 4 may be represented by IKBL promoter −63T/A. The G/C polymorphism at nucleotide 1228 of the nucleotide sequence of the promoter of the BAT1 gene shown in SEQ ID NO: 5 may be represented by BAT1 promoter −23G/C.

For example, as shown in the following Table 1, the onset of inflammatory diseases or the existence of a high probability of such onset can be determined when nucleotide 10 of the nucleotide sequence of exon 1 of the LT-α gene shown in SEQ ID NO: 1 is G (LT-α exon 1 10G), when nucleotide 90 of the nucleotide sequence of intron 1 of the LT-α gene shown in SEQ ID NO: 2 is A (LT-α intron 1 252A), when nucleotide 80 of the nucleotide sequence of exon 3 of the LT-α a gene shown in SEQ ID NO: 3 is C (LT-α exon 3 723C), when nucleotide 572 of the nucleotide sequence of the promoter of the IKBL gene shown in SEQ ID NO: 4 is A (IKBL promoter −63A), or when nucleotide 1228 of the nucleotide sequence of the promoter of the BAT1 gene shown in SEQ ID NO: 5 is G (BAT1 promoter −23G).

In contrast, a lack of onset of inflammatory diseases or the existence of a low probability of such onset can be determined when nucleotide 10 of the nucleotide sequence of exon 1 of the LT-α gene shown in SEQ ID NO: 1 is A (LT-α exon 1 10A), when nucleotide 90 of the nucleotide sequence of intron 1 of the LT-α gene shown in SEQ ID NO: 2 is G (LT-α intron 1 252G), when nucleotide 8480of the nucleotide sequence of exon 3 of the LT-α gene shown in SEQ ID NO: 3 is A (LT-α exon 3 723A), when nucleotide 572 of the nucleotide sequence of the promoter of the IKBL gene shown in SEQ ID NO: 4 is T (IKBL promoter 31 63T), or when nucleotide 1228 of the nucleotide sequence of the promoter of the BAT1 gene shown in SEQ ID NO: 5 is C (BAT1promoter −23C).

Moreover, LT-α expression levels differ depending on differences (10G-252A heterozygous, 10A-252G heterozygous, and 10A-252A homozygous) in combinations of nucleotide 10 of the nucleotide sequence of exon 1 of the LT-α gene shown in SEQ ID NO: 1 and nucleotide 90 (the $252^{nd}$ nucleotide when counted from the $1^{st}$ nucleotide of exon 1) of the nucleotide sequence of intron 1 of the LT-α gene shown in SEQ ID NO: 2. Therefore, inflammatory diseases can also be determined by detecting whether the combination of nucleotide 10 of the nucleotide sequence of exon 1 of the LT-α gene shown in SEQ ID NO: 1 and nucleotide 90 of the nucleotide sequence of intron 1 of the LT-α gene shown in SEQ ID NO: 2 is 10G-252A heterozygous, 10A-252G heterozygous, or 10A-252A homozygous.

For example, as shown in the following examples, in the case of 10A-252G, the LT-α expression level, the signal of inflammation, is significantly high and the onset of inflammatory diseases or the existence of a high probability of such onset can be determined.

Furthermore, the C/A polymorphism at nucleotide 80 of the nucleotide sequence of exon 3 of the LT-α gene shown in SEQ ID NO: 3 causes an amino acid mutation from threonine to asparagine because of a change at codon 26 (from ACC to AAC) in exon 3. For example, as shown in the following examples, in the case of codon 26 encoding asparagine (26N), the LT-α expression level is significantly higher than that in the case where codon 26 encodes threonine (26T), and vascular cell-adhesion molecule-1 (VCAM-1, the cell adhesion factor) and E-selectin are induced in human coronary-artery smooth-muscle cells (HCASMC). Thus, the onset of inflammatory diseases or the existence of a high probability of such onset can be determined.

In this specification, "determination" of diseases means to judge the presence or the absence of the onset of diseases, to judge (predict the risk of incidence) probabilities of the onset of diseases, to elucidate genetic factors of diseases, and the like.

"Determination" of diseases can be carried out by taking results obtained by the above method for detecting single nucleotide polymorphisms and results obtained by other polymorphism analyses (VNTR and RFLP) and/or other tests together, if desired.

Furthermore, in this specification, "inflammatory disease" is not specifically limited, as long as it is a disease confirmed to induce cell adhesion factors or cytokines that are known to correlate with pathologic conditions of inflammation. Examples of such inflammatory disease include chronic articular rheumatism, systemic erythematodes, inflammatory enteritis, various allergic reactions, bacterial shock, and arteriosclerotic diseases such as myocardial infarction and cerebral apoplexy. Particular examples include myocardial infarction.

(Detection Subject)

As subjects to be detected for gene polymorphisms, genomic DNA is preferable. In some instances (that is, when a polymorphic site and the sequence of a region adjacent thereto are identical to or completely complementary to a genome), cDNA or mRNA can also be used. Moreover, examples of a sample from which the above subjects are collected include any biological samples such as: body fluids such as blood, bone marrow fluids, sperm, peritoneal fluids, and urine; cells of tissues such as liver; and body hair such as hair. Genomic DNA and the like can be extracted, purified and prepared from such samples according to standard methods.

(Amplification)

Upon detection of gene polymorphisms, a region containing gene polymorphisms is first amplified. Amplification is carried out by, for example, the PCR method, or can also be carried out by other known amplification methods such as an NASBA method, an LCR method, an SDA method, and a LAMP method.

Primers are selected so that, for example, in the sequences shown in SEQ ID NOS: 1 to 5, sequences of at least 10 or more, preferably 10 to 100, and more preferably 10 to 50 continuous nucleotides containing the above single nucleotide polymorphism site(s), and/or complementary sequences thereof, are amplified.

A primer may also contain in its sequences one or more substitutions, deletions, or additions, as long as it can function as a primer for amplifying a sequence of a predetermined number of nucleotides containing the above single nucleotide polymorphism site(s).

Primers to be used for amplification may also be selected so that either a forward primer or a reverse primer hybridizes to a single nucleotide polymorphism site and amplification is conducted only when a sample is of a single allele type. Primers can be labeled with fluorescent substances, radioactive substances, or the like, if necessary.

(Detection of Polymorphisms)

Polymorphisms can be detected by hybridization with a probe that is specific to a single allele type. Probes may be labeled by appropriate means such as fluorescent substances or radioactive substances, if necessary. The probe is not specifically limited, as long as it contains the above single nucleotide polymorphism site(s), hybridizes to a test sample, and confers specificity detectable under detection conditions employed. As a probe, for example, sequences of at least 10 or more, preferably 10 to 100, and more preferably 10 to 50 continuous nucleotides containing the above single nucleotide polymorphism site(s) contained in the sequences shown in SEQ ID NOS: 1 to 5, or oligonucleotides capable of hybridizing to the complementary sequences thereof, can be used. Moreover, an oligonucleotide is preferably selected so that a single nucleotide polymorphism site exists at almost the central portion of the probe. The oligonucleotide may contain in its sequence one or more substitutions, deletions, or additions, as long as it can function as a probe; that is, as long as it can hybridize under conditions where it hybridizes to a sequence of a target allele type, but does not hybridize to sequences of other allele types. Examples of the probe include probes that satisfy the above probe conditions by annealing with genomic DNA to form a circle, such as a single-stranded probe (padlock probe) that is used for amplification by an RCA (rolling circle amplification) method.

Hybridization conditions employed in the present invention are conditions sufficient for distinguishing allele types. Examples of such conditions are stringent conditions wherein hybridization takes place when a sample is of a single allele type, but does not take place when a sample is of another allele type. Here, examples of "stringent conditions" include conditions described in Molecular Cloning: A Laboratory Manual ($2^{nd}$ edition, Sambrook et al., 1989). Specific examples of such conditions include conditions wherein a solution containing 6×SSC (1×SSC composition: 0.15 M NaCl, 0.015 M sodium citrate, pH 7.0), 0.5% SDS, 5×Denhardt, and 100 mg/ml Pacific herring sperm DNA and a probe are together incubated at 65° C. overnight.

A probe with its end fixed on a support can also be used as a DNA chip. In this case, onto the DNA chip, only a probe corresponding to a single allele type may be fixed, or a probe corresponding to both allele types may be fixed.

Gene polymorphisms can also be detected by a restriction enzyme fragment length polymorphism analytical method (RFLP: Restriction fragment length polymorphism). In this method, sample nucleic acids are digested with restriction enzymes (whether or not nucleic acids are cleaved by restriction enzymes depends on the genotype of a single nucleotide polymorphism site), and then the thus digested fragment sizes are examined to know whether or not the sample nucleic acids are cleaved with the restriction enzymes, whereby the polymorphisms of the sample are analyzed.

Gene polymorphisms may also be detected by directly sequencing amplified products (direct sequencing method). Sequencing can be carried out by a known method such as a dideoxy method or a Maxam-Gilbert method.

Gene polymorphisms may also be detected by an invader assay. In this method, an invader oligo that has a sequence complementary to a DNA target fragment to be tested to determine the presence or the absence of SNP and a complementary oligo (signal probe) that contains a 5'-flap structure and is used for detecting SNP are used. First an invader oligo and a signal probe are allowed to hybridize to a target DNA. At this time, the invader oligo and the probe form an invasive structure wherein they overlap at a single nucleotide. Cleavase (flap endonuclease separated from *Archaeoglobus fulgidus*) acts on this portion. When nucleotides of a signal probe at an SNP site and target nucleotides are complementary (no SNPs) to each other, the 5' flip of the signal probe is cleaved. The cleaved 5' flip hybridizes to a FRET (fluorescence resonance energy transfer) probe. On the FRET probe, a fluorescent dye and a quencher (Quencher) are closely adjacent to each other so as to suppress fluorescence. Binding of the 5' flip DNA results in cleavage of a portion of the fluorescent dye by cleavase, so that fluorescence signals can be detected.

Furthermore, to detect gene polymorphisms, a denaturing gradient gel electrophoresis (DGGE) method, single strand conformation polymorphism analysis (SSCP), allele-specific PCR, a hybridization method using ASO (allele-specific oligonucleotide), chemical cleavage of mismatches (CCM), an HET (heteroduplex method) method, a PEX (primer extension) method, an RCA (rolling circle amplification) method, or the like can be used.

[2] Kit for Diagnosing Inflammatory Diseases

A kit for diagnosing inflammatory diseases comprising the above primers or oligonucleotides as probes can be provided. The kit may also contain restriction enzymes, polymerase, nucleoside triphosphate, labels, buffers, and the like to be used for methods for analyzing the above polymorphisms.

[3] Method for Analyzing Expression State of LT-α, IKBL, or BAT1

According to the present invention, the expression state of LT-α, IKBL, or BAT1 can be analyzed by detecting at least one single nucleotide polymorphism selected from the group consisting of the above (1) to (5).

For example, it can be determined that the LT-α expression level is high when nucleotide 10 of the nucleotide sequence of exon 1 of the LT-α gene shown in SEQ ID NO: 1 is A and when nucleotide 90 (the 252nd nucleotide when counted from the 1st nucleotide of exon 1) of the nucleotide sequence of intron 1 of the LT-α gene shown in SEQ ID NO: 2 is G (10A-252G haplotype). In contrast, it can be determined that the LT-α expression level is low when nucleotide 10 of the nucleotide sequence of exon 1 of the LT-α gene shown in SEQ ID NO: 1 is G and nucleotide 90 (the 252nd nucleotide when counted from the 1st nucleotide of exon 1) of the nucleotide sequence of intron 1 of the LT-α gene shown in SEQ ID NO: 2 is A (10G-252A haplotype). Also, it can be determined that the LT-α expression level is low when nucleotide 10 of the nucleotide sequence of exon 1 of the LT-α gene shown in SEQ ID NO: 1 is A and nucleotide 90 (the $252^{nd}$ nucleotide when counted from the $1^{st}$ nucleotide of exon 1) of the nucleotide sequence of intron 1 of the LT-α gene shown in SEQ ID NO: 2 is A (10A-252A haplotype).

[4] Method for Measuring Transcriptional Activity of LT-α, IKBL, or BAT1

According to the present invention, the transcriptional activity of LT-α, IKBL, or BAT1 can be measured by introducing an LT-α, IKBL, or BAT1 gene fragment containing at least one single nucleotide polymorphism selected from the group consisting of the above (1) to (5) into a cell, culturing the cell, and analyzing the expression of the gene.

According to a preferred embodiment of the present invention, the expression of the gene is analyzed by introducing a transcriptional unit wherein a reporter gene is ligated downstream of the above LT-α, IKBL, or BAT1 gene fragment into a cell, culturing the cell, and measuring the reporter activity.

For example, when a single nucleotide polymorphism exists at a promoter site, a cell into which a system having a reporter gene inserted downstream of a gene containing the single nucleotide polymorphism has been introduced is cultured, and then the reporter activity is measured, so that differences in transcriptional efficiency due to the single nucleotide polymorphism can be measured.

As a reporter gene, a luciferase gene, a chloramphenicol gene, an acetyltransferase gene, a galactosidase gene, or the like may be used here.

[5] Method for Screening for Transcriptional Activity-Inhibiting Substance of LT-α, IKBL, or BAT1

In the present invention, an LT-α, IKBL, or BAT1 transcriptional-activity-inhibiting substance can be screened for by introducing an LT-α, IKBL, or BAT1 gene fragment containing at least one single nucleotide polymorphism selected from the group consisting of the above (1) to (5) into a cell, culturing the cell in the presence of a candidate substance that inhibits the transcriptional activity of LT-α, IKBL, or BATE, and analyzing the expression of the gene.

According to a preferred embodiment of the present invention, the expression of the gene is analyzed by introducing a transcriptional unit wherein a reporter gene is ligated downstream of the above LT-α, IKBL, or BAT1 gene fragment into a cell, culturing the cell, and measuring the reporter activity.

For example, a cell wherein a system having a reporter gene inserted downstream of a gene having a single nucleotide polymorphism (e.g., the above 10A-252G haplotype) confirmed to result in significantly high LT-α expression levels has been introduced is cultured in cases of both the presence and the absence of a candidate substance. If the resulting reporter activity decreases when the cell is cultured in the presence of the candidate substance, the candidate substance can be selected as an LT-α transcriptional-activity-inhibiting substance.

As reporter genes, the aforementioned genes are used.

As candidate substances, any substances can be used. Types of candidate substances are not specifically limited. Such candidate substances may be individual low molecular synthetic compounds, or compounds that are present in extracts from natural substances. Alternatively, they may be compound libraries, phage display libraries, or combinatorial libraries. Preferably a candidate substance is a low molecular weight compound, and a compound library of low molecular weight compounds is preferable. Construction of such a compound library is known to persons skilled in the art. Furthermore, commercial compound libraries can also be used.

LT-α, IKBL, or BAT1 transcriptional-activity-inhibiting substances obtained by the above screening method are also encompassed in the scope of the present invention. Such LT-α, IKBL, or BAT1 transcriptional-activity-inhibiting substances are useful as candidate substances for various drugs such as myocardial infarction therapeutic agents, antiinflammatory agents, and immunosuppressants.

[6] Method for Screening for LT-α Transcriptional Regulatory Factor

Furthermore, in the present invention, a transcriptional regulatory factor of LT-α, IKBL, or BAT1 can be screened for by bringing a gene fragment containing at least one single nucleotide polymorphism selected from the group consisting of the above (1) to (5) into contact with a sample wherein a transcriptional regulatory factor of LT-α, IKBL, or BAT1 is presumed to be present, and detecting the binding of the above fragment with the transcriptional regulatory factor. Such binding of a gene fragment containing the above single nucleotide polymorphism with a substance wherein a transcriptional regulatory factor of LT-α, IKBL, or BAT1 is presumed to be present can be detected by a gel-shift assay (electrophoretic mobility shift assay, EMSA), DNase I footprinting method, or the like. The gel-shift assay is preferable. In the gel shift method, when a protein (transcriptional regulatory factor) binds, the resulting molecular size becomes larger so as to lower the mobility of DNA in electrophoresis. Thus, a $^{32}$p-labeled gene fragment and a transcriptional regulatory factor are mixed, and then the resultant is subjected to gel electrophoresis. When the position of DNA is visualized by autoradiography, the shift of the factor-bound DNA is slow, so that it is detected as a band that shifts behind normal bands.

[7] Method for Treating Inflammatory Disease and Therapeutic Agent for Inflammatory Disease In the present invention, as shown in the following Example 5, when the expression state of LT-α protein in torose lesions of arterial walls was examined, the LT-α protein in vascular smooth-muscle cells in the torose lesions of the arterial walls and macrophages from myocardial infarction patients, were stained intensely, suggesting possible association of the protein with generation and development of the lesion. Hence, it can be expected that such lesion can be healed to some extent or the recurrence thereof can be prevented by suppressing the expression or activity of LT-α protein.

Figure 5:
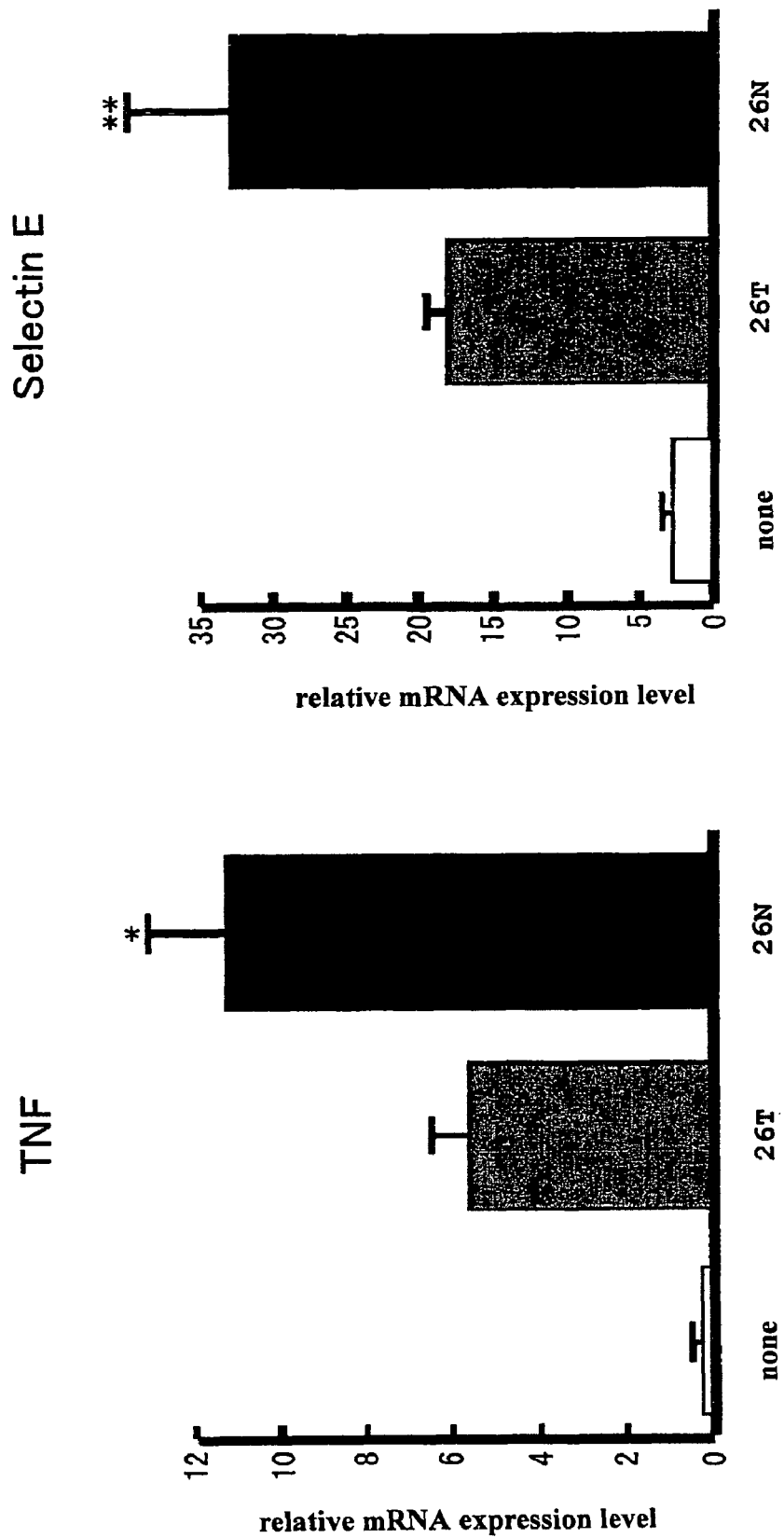
FIG. 5 shows the results of comparing LT-α(26Asn)(26N) with LT-α(26Thr)(26T) for TNF-inducing activity and Selectin E-inducing activity (relative mRNA expression level) in human coronary-artery endothelial cells (HCAEC). Results show the mean±S.D. (*p<0.01, and **p<0.05 versus 26T).
Figure 6:
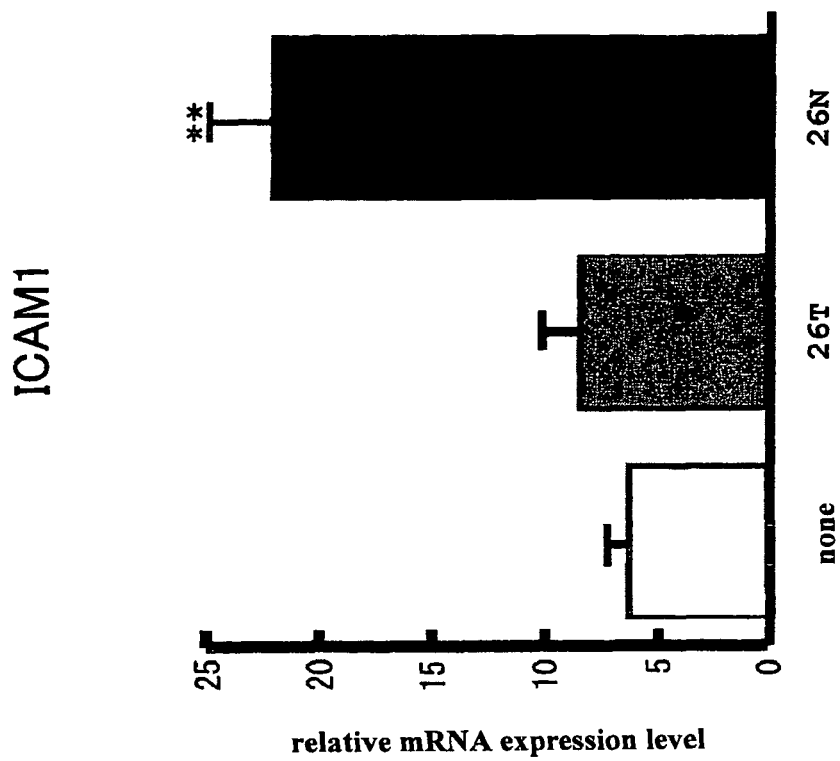
FIG. 6 shows the results of comparing LT-α(26Asn)(26N) with LT-α(26Thr)(26T) for TNF-inducing activity and ICAM1-inducing activity (relative mRNA expression level) in a hemocytic cell line (HL-60). Results show the mean±S.D. (*p<0.01 versus 26T).
Figure 6:
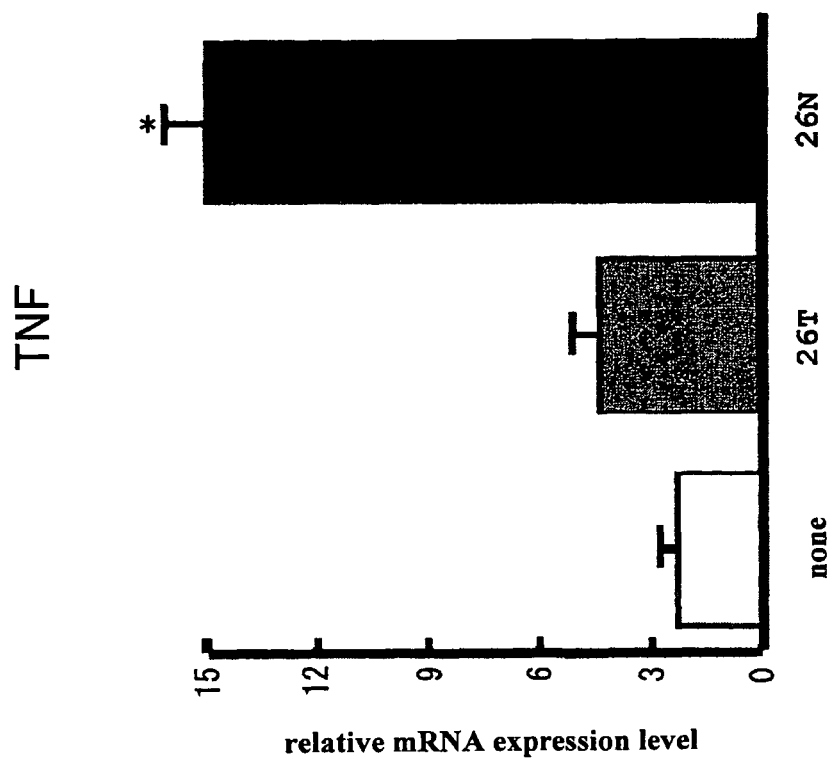

Furthermore, an LT-α 26Asn variant that is a myocardial-infarction-susceptibility gene product is known to have stronger ability to induce adhesion molecules (VCAM-1 and E-selectin) from vascular smooth-muscle cells as compared with that of a wild type (26Thr) (Ozaki k. et al. Nature Genetics 32, 650-654, 2002). In the present invention, as shown in the following Example 6, the LT-α variant (26Asn) was compared with 26Thr for cytokine-inducing activity and adhesion-molecule-inducing activity in human coronary-artery endothelial cells (HCAEC) and in a hemocytic cell line (HL-60). As a result, as shown in FIGS. 5 and 6, LT-α (26Asn) induced twice as much tumor necrosis factor-α (TNF) and selectin-E mRNA from vascular endothelial cells and induced three times as much TNF and ICAM-1 (intracellular cell adhesion molecule-1) mRNA from HL-60 cells, as compared with LT-α (Thr26). These results show the association of LT-α (26Asn) with the onset and development of inflammatory diseases such as myocardial infarction. Furthermore, it can be expected that inflammatory diseases such as myocardial infarction can be treated by suppressing LT-α activity. Moreover, as a means for suppressing LT-α activity, for example, an antibody against lymphotoxin-α (LT-α) can be used.

Furthermore, therapeutic agents for inflammatory diseases comprising as an active ingredient a substance that suppresses the expression or activity of lymphotoxin-α (LT-α) are also encompassed within the scope of the present invention. An example of a substance that suppresses the expression or activity of lymphotoxin-α (LT-α) used herein is an antibody against lymphotoxin-α. Moreover, as an antibody against lymphotoxin-α, a human antibody or a humanized antibody can also be used.

Antibodies against lymphotoxin-α can be prepared by standard methods. For example, polyclonal antibodies against lymphotoxin-α can be obtained by immunizing mammals (e.g., mice, rats, rabbits, goats, sheep, or cattle) by a method known to persons skilled in the art using lymphotoxin-α as an antigen, collecting blood from the mammals, and separating and purifying antibodies from the collected blood. When an antigen is administered, an appropriate adjuvant can also be used. Antibodies can be separated and purified from blood by general methods such as centrifugation, precipitation using ammonium sulfate or polyethylene glycol, and chromatography such as gel filtration chromatography, ion exchange chromatography, and affinity chromatography.

Monoclonal antibodies against lymphotoxin-α can be prepared using hybridomas. Hybridomas producing monoclonal antibodies against lymphotoxin-α can be prepared by fusing antibody-producing cells (e.g., spleen cells, lymph node cells, and B-lymphocytes collected from immunized animals) with myeloma cells (e.g., in the case of mouse, P3X63Ag8, P3U1 line, and Sp2/0 line) using a fusion promoter such as polyethylene glycol or Sendai virus. For selection of hybridomas after cell fusion, hypoxanthine aminopterin thymidine (HAT) media can be used according to standard methods. To produce a monoclonal antibody of interest from the thus obtained hybridomas, the hybridomas may be cultured by general cell culture methods or ascite formation methods, and then the monoclonal antibody may be purified from the resulting culture supernatant or ascite.

[8] Method for Screening for Therapeutic Agent for Inflammatory Disease

As described above, in the present invention, it was shown that the enhanced expression or activity of lymphotoxin-α is associated with inflammatory diseases. Thus, it was revealed that substances lowering the expression or activity of lymphotoxin-α are useful as therapeutic agents for inflammatory diseases. According to the present invention, there is further provided a method for screening for a substance that lowers the expression or activity of lymphotoxin-α. An example of the above screening method can be carried out with the steps of: bringing a cell into contact with a candidate substance; analyzing the expression level of a gene encoding lymphotoxin-α (LT-α) within the cell; and selecting as a therapeutic agent for an inflammatory disease a candidate substance that lowers the expression level of the gene more than a condition wherein the candidate substance is absent. Another example of the above screening method can be carried out with the steps of: bringing lymphotoxin-α (LT-α) into contact with a candidate substance; measuring the LT-α activity; and selecting as a therapeutic agent for an inflammatory disease a candidate substance that lowers the lymphotoxin-α activity more than a condition wherein the candidate substance is absent. "Lymphotoxin-α activity" used herein is, for example, activity to induce adhesion molecules and/or cytokines. Specific examples of adhesion molecules include VCAM-1, ICAM-1, or E-selectin. A specific example of a cytokine is TNF.

As candidate substances, any substances can be used. Types of candidate substances are not specifically limited. For example, various libraries and the like described in [5] above in this specification can be used.

The present invention is explained more specifically by the following examples, but the present invention is not limited by these examples.

EXAMPLES

Example 1

Association Study

[1] Method

1. Subject

In general, the diagnosis of myocardial infarction requires two of the following three criteria: (1) clinical history of central chest pressure, pain, or tightness lasting for 30 minutes or more; (2) ST-segment elevation greater than 0.1 mV in at least one standard or two precordial leads; and (3) a rise in serum creatine kinase concentration to greater than twice the normal laboratory value. 1,133 patients diagnosed as having myocardial infarction based on these criteria were subjected to the study. The ages of the subjects with myocardial infarction ranged from 28 to 85 years old, and the mean age was 62.5 years old. In the meantime, 1,006 healthy subjects who had applied for this study through some medical institutions were subjected to the study as controls. The ages of the control subjects ranged from 5 to 88 years old and the mean age was 38.5 years old. In addition, all subjects were Japanese.

2. SNP Discovery and Genotyping

For a whole-genome association study, an SNP database that is available on website (http://snp.ims.u-tokyo.ac.jp) was used. Screening of SNPs was performed as described previously (Iida, A., et al., J. Hum. Genet., 46, 668-683, 2001). Screening was performed for approximately 130 kb of the relevant region on 6p21 (FIG. 1, upper panel) containing LT-α, TNF-α, LST1, 1C7, allograft inflammatory-factor-1 (AIF-1), I kappa B-like protein (IKBL), V-ATPase G-subunit like protein (ATP6G), BAT1, MICB, and p5-1. Before screening, a reference sequence of approximately 130 kb was generated by assembling sequences Y14768, AP000506, and AC004184 from the GeneBank database. Protocols for PCR primer design, PCR experiment, DNA extraction, DNA sequencing, and SNP discovery were in accordance with the description given in Iida, A., et al., J. Hum. Genet., 46, 668-683, 2001. SNPs in the 130-kb region were genotyped according to previous reports (Ohnishi, Y., et al., J. Hum. Genet., 46, 471-477, 2001; Iida, A., et al., J. Hum. Genet., 46, 668-683, 2001) by invader assay or direct sequencing of PCR products using a capillary sequencer (ABI 3700, Applied Biosystems).

The primers and probes used in this example are as shown below.

(1) LT-α (typing by the invader method)

PCR primer

```
Forward primer:
ACTCAGCCAAGGGTGCAGAG          (SEQ ID NO: 9)

Reverse primer:
CTTCCTCAGGGATTGAGACCTC        (SEQ ID NO: 10)
```

Probe (SNPs are put in square brackets)

```
Exon 1 10G>A
                              (SEQ ID NOS: 11 and 12)
TCCAAAGCACGAAGCACGGGCAGCCCAAGGAGATGGGGCAGGAGAGCCTC
ACCTGCTGTG[CT]GGAGCCCCTGGGCCCGGACGCTCAGGTCCCTTTATA
GAGGAAGCGGCAGTGGCAGCGTGG Intron 1 90A>G
                              (SEQ ID NOS: 13 and 14)
AGAGAAACCCCAAGGTGAGCAGAGGGAGACAGAGAGAGACAGGAAGGGAA
CAGAGAGGAA[TC]CATGGCAGAAACAGAGAATGTGTGACAGAGACAATG
AGACTGACAGATGGAGAGTCAGAG Exon 3 80C>A
                              (SEQ ID NOS: 15 and 16)
TCACACCTTCAGCTGCCCAGACTGCCCGTCAGCACCCCAAGATGCATCTT
GCCCACAGCA[CA]CCTCAAACCTGCTGCTCACCTCATTGGTAAACATCC
ACCTGACCTCCCAGACATGTCCCC
```

(2) IKBL (typing by the sequencing method)

PCR primer

```
Forward primer:
TTTAAGGCTCAGGAGCCCAG         (SEQ ID NO: 17)

Reverse primer:
TCCCTGTTGTTGTCCCACTG         (SEQ ID NO: 18)

Sequence primer:
ATATCATGTACCCGGCAGAC         (SEQ ID NO: 19)
```

(3) BAT1 (typing by the invader method)

PCR primer

3. Statistical Analysis

```
Forward primer:
                             (SEQ ID NO: 20)
TGGTCTCACATCACTGTTACGC Reverse primer:
                             (SEQ ID NO: 21)
TCTTCCCGCTCGGATTCAG Probe:
                             (SEQ ID NOS: 22 and 23)
AAGCTTACCTAAACAGGGAGAGCGCGTATGGCGGCAGCAACAGCGACGAA
GGAGGGAAAT[GC]TGCCTTCACTTCCGGTTGCAGGCTTCCCTCTACTCC
AGCCTCCCGCCTTCTTGGCTGCAA
```

Statistical analyses for the association study, haplotype frequencies, Hardy-Weinberg equilibrium, and calculation of LD coefficients (D') were performed according to a previous report (Yamada, R., et al., Am. J. Hum. Genet, 68, 674-485, 2001).

(2) Experimental Results

As the first step of the association study, 94 myocardial infarction patients were genotyped using the high-throughput multiplex PCR-invader assay method (Ohnishi, Y., et al., J. Hum. Genet., 46, 471-477, 2001), and the results were compared with the allelic frequencies found in the population of healthy subjects. As a result of screening for SNPs based on approximately 75,000 genes, a modest association of one SNP (intron 1; 252A>G) in the LT-α gene on chromosome 6p21 with myocardial infarction could be identified ($\chi^2$=9.4, p=0.0022; homozygotes for the minor allele versus others). As a result of subsequent genotyping of a total of 1,133 myocardial infarction patients and 1,006 control subjects, the association became much more significant, with a $\chi^2$ value of 18.0 (p=0.000022; homozygotes for the minor allele versus others) and an odds ratio of 1.69 (95% confidence interval (CI); 1.32 to 2.15, Table 1). These data indicated that a gene conferring susceptibility to myocardial infarction was present within this region.

A high-density SNP map for LD mapping was constructed by direct sequencing of DNAs from 16 myocardial infarction patients and 16 control subjects. Approximately 130 kilobases of the relevant region on 6p21 including several other molecules encoding molecules related to TNF-α, LT-β, I kappa B-like protein (IKBL), and BAT1 (FIG. 1, upper panel) were subjected to screening. A total of 187 SNPs were identified in the region. 94 myocardial infarction patients and 94 control subjects from a general population were genotyped for 120 of such markers, selected on the basis of allele frequencies greater than 10% (estimated roughly by comparison of the peak levels of nucleotide signals on the electropherogram). Finally, 26 SNPs with allele frequencies that were sufficiently high to identify a target gene as a gene associated with a disease (>25%, minor alleles) revealed one extended block of intense LD with D' drop-off near p5-1 and AIF-1 (FIG. 1, lower panel). Therefore, it was concluded that the myocardial-infarction-susceptibility gene was located between these two loci. These 26 SNPs were typed by expanding sample size. Although most of them showed no significant association with the myocardial infarction phenotype, four of these 26 SNPs revealed a tight association with myocardial infarction when the frequencies of homozygosity for the minor allele of the myocardial infarction patients and the control subjects were compared (Table 1). These SNPs were 10G>A in exon 1 and 723C>A (Thr26Asn) in exon 3 of LT-α, −63T>A in the promoter region of IKBL, and −23G>C in the promoter region of BAT1. All four SNPs were almost completely linked with each other and particular haplotypes in the region showed higher statistical significance for association with myocardial infarction than of the case of each SNP alone. The Hardy-Weinberg equilibrium of the distribution of genotypes for each SNP was evaluated by $\chi^2$ tests for both the patient group and the control group, showed no significant deviation (p>0.01). As these SNP loci had almost the same degree of association with myocardial infarction, it was concluded LT-α, IKBL, and BAT1 were all candidates for influencing susceptibility to myocardial infarction.

TABLE 1

Association of SNPs in LT-α, IKBL, and BAT1 with myocardial infarction

| Genotype | Myocardial infarction (N = 1,133) | Control (N = 1,006) | $\chi^2$ [p value] | OR (95% CI) |
|---|---|---|---|---|
| LT-α exon1 10 G > A | | | | |
| GG | 416(36.7%) | 378(37.6%) | | |
| GA | 504(44.5%) | 512(50.9%) | AA vs. GG + GA | 1.78 |
| AA | 213(18.8%) | 116(11.5%) | 21.6 [0.0000033] | (1.39-2.27) |
| LT-α intron1 252 A > G | | | | |
| AA | 413(36.5%) | 371(36.9%) | | |
| AG | 511(45.1%) | 516(51.3%) | GG vs. AA + AG | 1.69 |
| GG | 209(18.4%) | 119(11.8%) | 18.0 [0.000022] | (1.32-2.15) |
| LT-α exon3 723 C > A, T26N | | | | |
| CC | 414(36.5%) | 374(37.2%) | | |
| CA | 506(44.7%) | 516(51.3%) | AA vs. CC + CA | 1.78 |
| AA | 213(18.8%) | 116(11.5%) | 21.6 [0.0000033] | (1.39-2.27) |

TABLE 1-continued

Association of SNPs in LT-α, IKBL, and BAT1 with myocardial infarction

| Genotype | Myocardial infarction (N = 1,133) | Control (N = 1,006) | $\chi^2$ [p value] | | OR (95% CI) |
|---|---|---|---|---|---|
| IKBL promoter −63 T > A | | | | | |
| TT | 406(35.8%) | 374(37.2%) | | | |
| TA | 521(46.0%) | 509(50.6%) | | AA vs. TT + TA | 1.6 |
| AA | 206(18.2%) | 123(12.2%) | 14.5 [0.000129] | | (1.25-2.03) |
| BAT1 promoter −23 G > C | | | | | |
| GG | 411(36.3%) | 374(37.2%) | | | |
| GC | 517(45.6%) | 510(50.7%) | | CC vs. GG + GC | 1.6 |
| CC | 205(18.1%) | 122(12.1%) | 14.7 [0.000129] | | (1.26-2.04) |

Example 2

Increase in Transcriptional Activity Brought About by SNP in Intron 1 of LT-α

(1) Experimental Method

DNA fragments corresponding to −307 to 268 of LT-α, −635 to 15 of IKBL, and −1231 to 30 of BAT1 were amplified by PCR using genomic DNA as template, and cloned in pGL3-basic vector (Promega) in the 5'-3' orientation. Jurkut cells (obtained from RIKEN Cell Bank; RCB0806) were grown in a RPMI1640 medium supplemented with 10% fetal bovine serum. To determine whether the two SNPs in the LT-α gene, 10G>A in exon 1 and 252A>G in intron I, would affect its expression level, three kinds of plasmids with a genomic fragment containing both SNPs (10G-252A, 10A-252G, and 10A-252A haplotype) upstream of a luciferase gene transcriptional unit, were constructed.

The above Jurkut cells (2×10⁶) were transfected with 10 μg of the above plasmid construct and 2.5 μg of pRL-TK vector (internal control for transfection efficiency) using a Lipo-TAXI transfection reagent (Stratagene). 6 hours later, the cells were stimulated with PMA (20 ng/ml) and isonomycin (1 μM) (Sigma). 24 hours later, the cells were collected and then luciferase activity was measured using a Dual-Luciferase Reporter Assay System (Promega).

Furthermore, the influence of SNPs in the promoter regions of IKBL and BAT1 genes on transcriptional efficiency was examined similarly.

(2) Experimental Results

Figure 2:
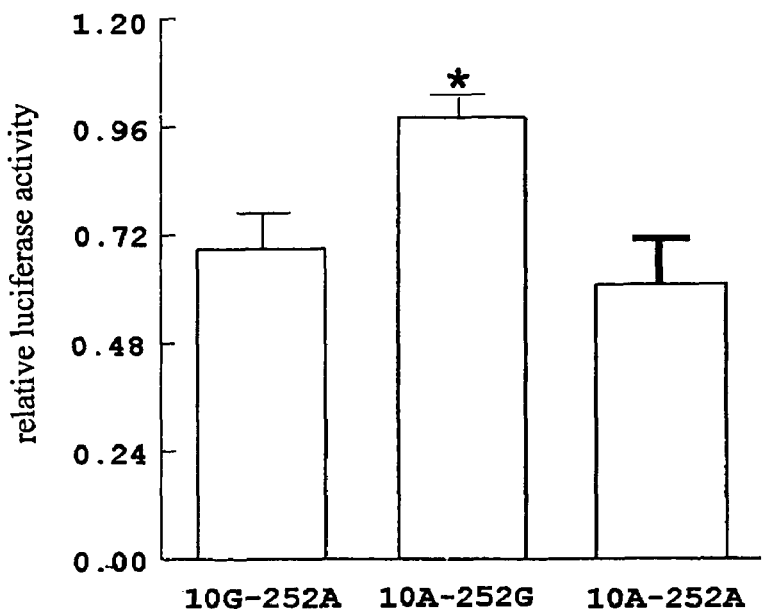
FIG. 2(A) shows transcriptional regulatory activity affected by SNPs in intron 1 (252A>G) of LT-α.
FIG. 2(B) shows the same within the promoter region (−63T>A) of IKBL. * p<0.01 in comparison between 10G-252A and 10A-252G: ** p<0.01 in comparison between −63A allele and −63T allele (student's t-test).
Figure 2:
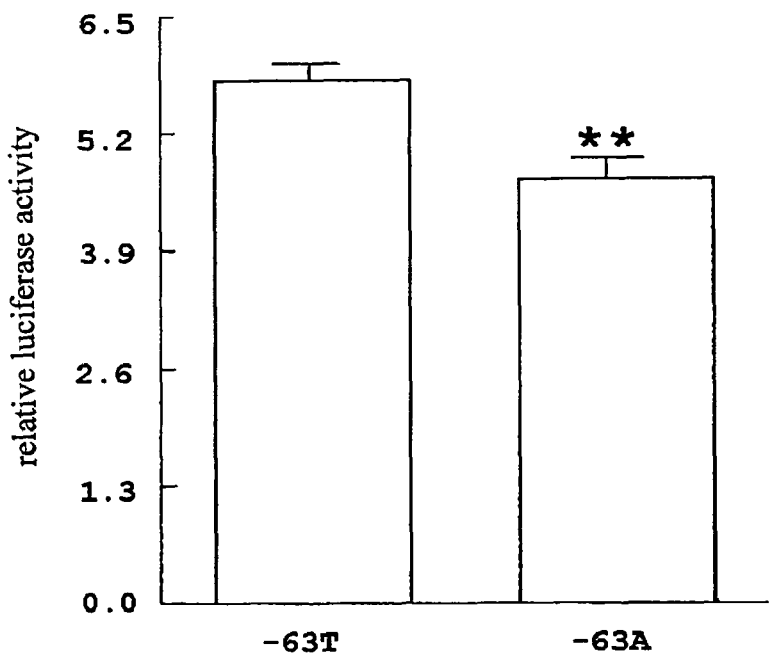

As shown in FIG. 2A, the clone containing the 10A-252G haplotype showed 1.5 fold greater transcriptional activity than clones containing the other two haplotypes, indicating that the substitution in intron 1, but not the one in exon affected transcription in an LT-α gene. Specifically, it was revealed that these 2 SNPs in the LT-α gene showing strong association with myocardial infarction affect the expression level.

In the meantime, for SNP in the promoter region of IKBL (−63T>A) similarly showing significant association with myocardial infarction, a moderate reduction was observed in transcriptional activity (FIG. 2B). IKBL is a member of the IkB family and an inhibitory molecule for transcription factors such as NF kappa B (NF-κB)/rel potein (Albertella, M. R., et al., Hum. Mol. Genet., 3, 793-799, 1994). Judging from the fact that DNA sequences in the LT-α promoter region contain binding motifs for several kinds of nuclear factors including NF-κB, SP-1, and AP-1/c-fos/jun (Messer, G. et al., J. Exp. Med., 173, 209-219, 1991), IKBL should be able to control LT-α transcription through inhibition of these nuclear factors.

Example 3

Binding of Unknown Nuclear Factor to LT-α Intron 1

(1) Experimental Method

Whether or not nuclear extracts from Jurkut cells can bind to oligonucleotides corresponding to genomic sequences containing a 252A or 252G allele was examined. As described in Andrews, N. C. et al., Nucleic, Acid Res., 11, 2499, 1991, nuclear extracts prepared from Jurkut cells were incubated with a 33-bp oligonucleotide labeled with digoxigenin (DIG)-11-ddUTP using a DIG-gel shift kit (Roche). For competitive study, an unlabeled oligonucleotide (100-fold excess) was pre-cultured with the nuclear extract before addition of DIG-labeled oligonucleotide. The protein/DNA complexes were separated on a non-denaturing 7% polyacrylamide gel in a 0.5×Tris/Borate/EDTA (TBE) buffer. The gel was transferred to a nitrocellulose membrane, and detection of the signal was performed with a chemiluminescent detection system (Roche) according to the manufacturer's instructions.

(2) Experimental Results

Figure 3:
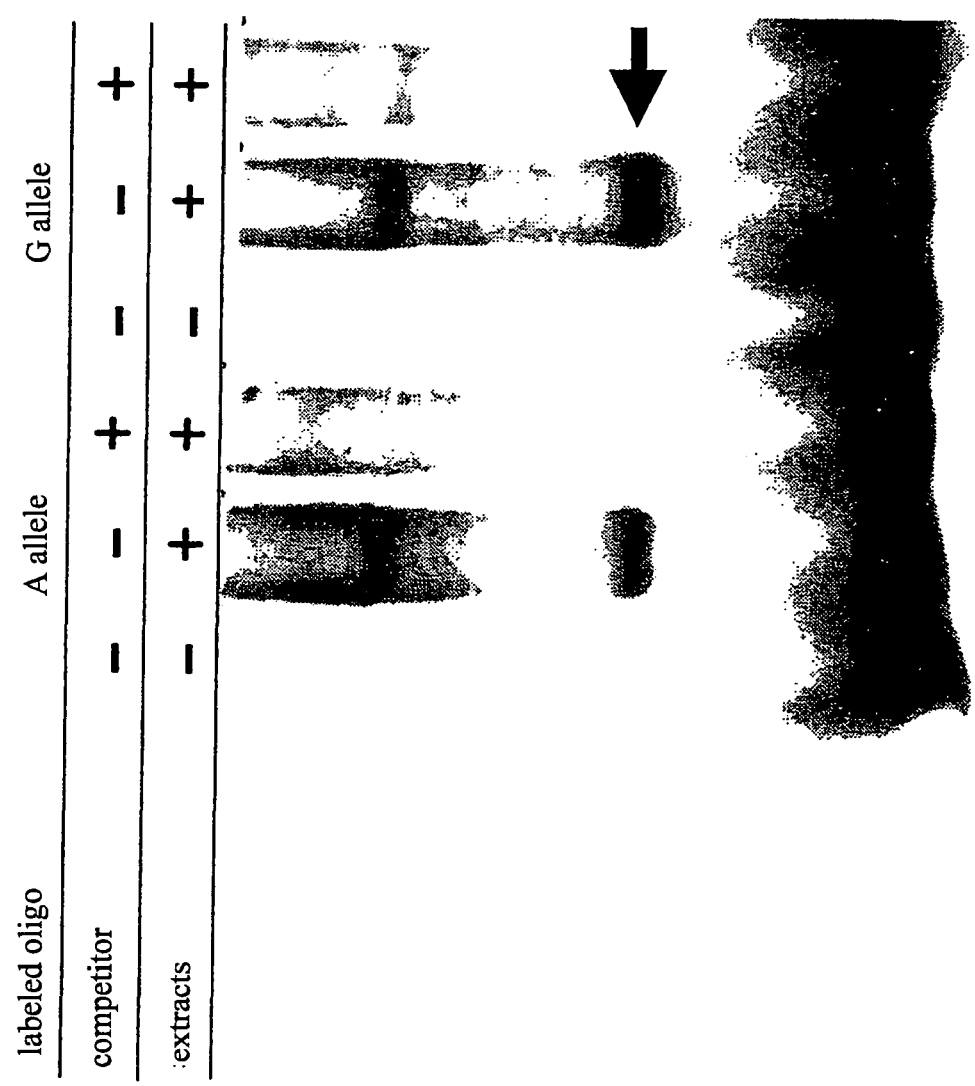
FIG. 3 shows binding of unknown nuclear factor(s) to intron 1 of LT-α. An arrow indicates the band showing tighter binding of nuclear factor(s) to the G-allele.

As shown in FIG. 3, the band that appeared when the oligonucleotide corresponding to the G allele was used was more intense than the band corresponding to the A allele, indicating that some nuclear factor present in Jurkat cells was binding more tightly to the G allele than to the A allele. The experiment was conducted 3 times and similar results were obtained. These results indicated that one or more unidentified molecules in the nuclear extracts, which regulate the transcription of LT-α by binding to this region, may be associated with myocardial infarction.

Example 4

Induction of Adhesion Molecule by T26N Variation in LT-α Protein (1) Experimental Method The LT-α product can induce adhesion molecules and cytokines from vascular endothelial cells, vascular smooth-muscle cells, and several kinds of leucocytes, as its contribution to the inflammatory process (Ross, R., N. Engl. J. Med., 340, 115-126, 1999; Ware, C. F., et al., Curr. Top. Microbiol. Immunol., 198, 175-218, 1995). Whether these biological activities could be influenced by the amino-acid substitution in the gene product was examined. SNP at codon 26 results in amino acid change from threonine to asparagine. The ability of each allele (26N-LT-α or 26T-LT-α) to induce the expression of adhesion molecules and cytokines was examined as follows using cultured human coronary-artery endothelial cells (HCAEC) and cultured human coronary-artery smooth-muscle cells (HCASMC).

First, purified *Escherichia coli*-derived recombinants (26N-LT-α and 26T-LT-α) were prepared using a pET43 system (Novagen). HCAEC and HCASMC (BioWhittaker, Inc.) were treated with 5 ng/ml LT-α protein (26N-LT-α or 26T-LT-α) for 4 hours. Total RNA was isolated using trizol (Life Technologies). cDNA was prepared from 2 µg of total RNA by $dT_{15}$ priming and synthesized using SuperScript reverse transcriptase (Life Technologies). mRNA was quantified using the QuantiTect SYBR Green PCR kit (QIAGEN) and an ABI Prism 7700 sequence detector (Applied Biocystems). Each experiment was repeated three times and each sample was tested in triplicate.

(2) Experimental Results

Figure 4:
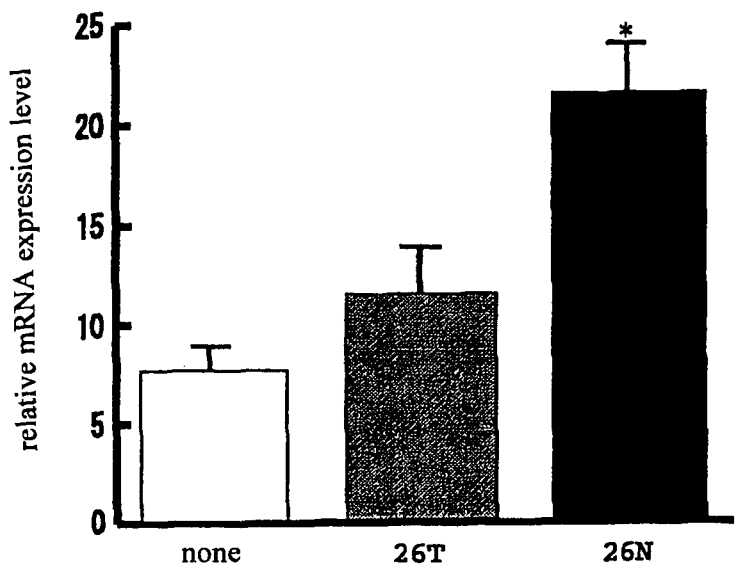
FIG. 4(A) shows relative mRNA expression levels of VCAM-1 obtained in a case where only HCASMC was cultured (white bar) and the same in a case where HCASMC was treated for 4 hours using 26T-LT-α (gray bar) or 26N-LT-α (black bar) (5 ng/ml) and cultured.
FIG. 4(B) shows relative mRNA expression levels of E-selectin obtained in a case where only HCASMC was cultured (white bar) and the same in a case where HCASMC was treated for 4 hours using 26T-LT-α (gray bar) or 26N-LT-α (black bar) (5 ng/ml) and cultured. Results show the mean±S.D. (n=3, *p<0.01, and **p<0.05 versus 26T).
Figure 4:
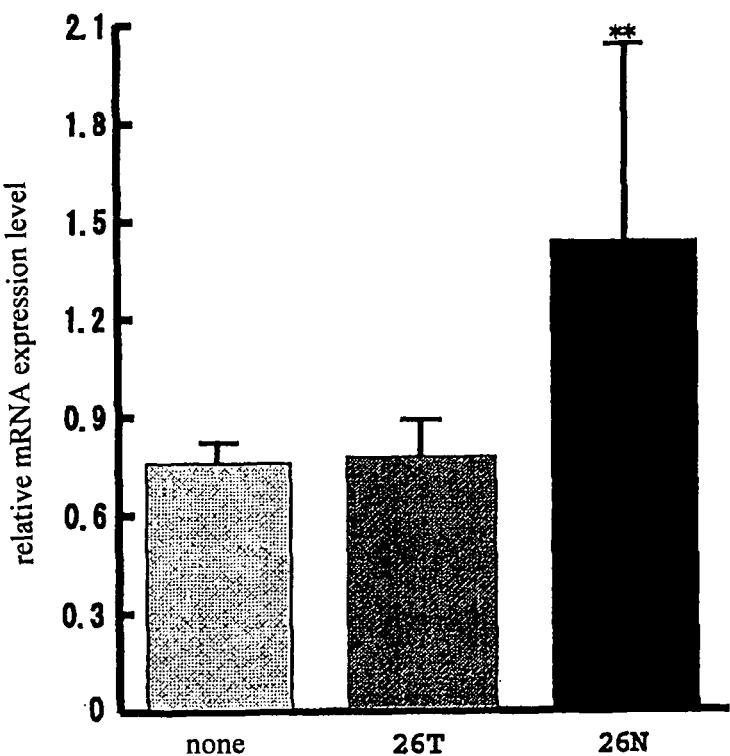

The variant protein, 26N-LT-α, showed a level of transcriptional activity that was 2 times higher than that shown by 26T-LT-α in HCASMC for vascular cell adhesion molecule-1 (VCAM-1) and E-selectin mRNA (FIG. 4).

Example 5

Expression State of LT-α Protein in Torose Lesion of Arterial Wall (1) Experimental Method Paraffin-embedded sections of torose lesions of arterial walls were attached on silane coating slides, followed by deparaffinization using xylene. Subsequently, antigenicity was activated with a microwave. To inhibit endogenous peroxidase activity, treatment was carried out using a 3% hydrogen peroxide solution/ethanol for 15 minutes. To suppress non-specific reaction, blocking reaction was carried out with a 5% skim milk solution. Reaction was conducted at 40° C. overnight using 5 µg/ml anti-LT-α antibody (R & D). After washing, a secondary antibody (rabbit ENVISION Polymer Reagent; DAKO) was added, followed by 1 hour of reaction at room temperature. After color development using a peroxidase substrate, the LT-α protein signal was observed under a microscope. As a negative control, a sample was stained similarly using non-immune normal sheep IgG (DAKO).

(2) Experimental Results

As a result of the above immunostaining, it was confirmed that LT-α protein was intensely stained in vascular smooth-muscle cells within the torose lesions of the arterial walls and macrophages derived from myocardial infarction patients. The results suggested possible involvement of LT-α protein in generation and development of such lesions.

Example 6

Induction of Cytokine and Adhesion Molecule from Vascular Endothelial Cell and Hemocytic Cell Line by LT-α Variant (Asn26)

(1) Experimental Method

Coronary-artery endothelial cells (Bio Whittaker) were cultured in media specially used for vascular endothelial cells (Bio Whittaker), and HL-60 (RIKEN cell BANK) was cultured in RPMI-1640 media (SIGMA). Preparation of LT-α protein and evaluation of induction of cytokines and adhesion molecule mRNA were carried out according to a previous report (Ozaki k. et al. Nature Genetics 32, 650-654, 2002).

(2) Experimental Results

For the activity to induce cytokines and adhesion molecules in human coronary-artery endothelial cells (HCAEC) and a hemocytic cell line (HL-60), LT-α (26Asn) was compared with LT-α (26Thr). The results are shown in FIGS. 5 and 6. As shown in FIGS. 5 and 6, LT-α (Asn26) induced twice as much tumor necrosis factor-α (TNF) and selectin-E mRNA from vascular endothelial cells, and induced 3 times as much TNF and ICAM-1 (intracellular cell adhesion molecule-1) mRNA from HL-60 cells than LT-α (Thr26). These results showed involvement of LT-α (26Asn) in the onset and development of inflammatory diseases such as myocardial infarction.

INDUSTRIAL APPLICABILITY

According to the method of the present invention, judgment of the presence or the absence of the onset of inflammatory diseases such as myocardial infarction and judgment of the probability of the onset of the disease can be performed accurately and rapidly.

The invention claimed is:

1. A method for determining an increased risk of myocardial infarction in humans, which comprises detecting an A/A homozygous genotype at nucleotide 80 in the nucleotide sequence of exon 3 of the LT-α gene shown in SEQ ID NO: 3, wherein the presence of the A/A homozygous genotype is indicative of increased risk of myocardial infarction.

2. The method according to claim 1, which comprises use of an oligonucleotide as a probe that can hybridize to a sequence of at least 10 continuous nucleotides containing position 80 of the nucleotide sequence of exon 3 of the LT-α gene shown in SEQ ID NO: 3 or to a complementary sequence thereof.

3. The method according to claim 1, which comprises use of an oligonucleotide as a primer that can amplify a sequence of at least 10 continuous nucleotides containing position 80 of the nucleotide sequence of exon 3 of the LT-α gene shown in SEQ ID NO: 3 and/or to a complementary sequence thereof.

4. The method according to claim 3 wherein the primer is forward primer and/or reverse primer.

* * * * *

SEQUENCE LISTING

```
<160> NUMBER OF SEQ ID NOS: 23

<210> SEQ ID NO 1
<211> LENGTH: 162
<212> TYPE: DNA
<213> ORGANISM: Homo sapiens

<400> SEQUENCE: 1
aggggctccg cacagcaggt gaggctctcc tgccccatct ccttgggctg cccgtgcttc      60
gtgctttgga ctaccgccca gcagtgtcct gccctctgcc tgggcctcgg tccctcctgc     120
acctgctgcc tggatccccg gcctgcctgg gcctgggcct tg                        162
```

<210> SEQ ID NO 2
<211> LENGTH: 287
<212> TYPE: DNA
<213> ORGANISM: Homo sapiens

<400> SEQUENCE: 2

```
gtgggtttgg ttttggtttc cttctctgtc tctgactctc catctgtcag tctcattgtc      60
tctgtcacac attctctgtt ctgccatga ttcctctctg ttcccttcct gtctctctct       120
gtctccctct gctcaccttg gggtttctct gactgcatct tgtccccttc tctgtcgatc      180
tctctctcgg gggtcggggg gtgctctctc ccagggcggg aggtctgtct tccgccgcgt      240
gccccgcccc gctcactgtc tctctctctc tctctctttc tctgcag                   287
```

<210> SEQ ID NO 3
<211> LENGTH: 106
<212> TYPE: DNA
<213> ORGANISM: Homo sapiens

<400> SEQUENCE: 3

```
gggctccctg gtgttggcct cacaccttca gctgcccaga ctgcccgtca gcaccccaag      60
atgcatcttg cccacagcac cctcaaacct gctgctcacc tcattg                    106
```

<210> SEQ ID NO 4
<211> LENGTH: 634
<212> TYPE: DNA
<213> ORGANISM: Homo sapiens

<400> SEQUENCE: 4

```
caacctgtgt tgggaaaaga gcattctggg cttaattcta aactaactct ctacctttct      60
ctctctctcc accatcccgc cccctcccct gcctcccgtt gttaacatct ccatcttttt     120
ctacatattt ctcaagtcca aattttttgca tctcacttgc cccatcctac gatagtcttc    180
ttccgtcttt tgtctgtatt ttttcttttt tttgatctgt ccctgttgtt gtcccactgt     240
ggttttttgtt tttgttttcc atgtttaatg tgatttttat cctgtcttta tctcctctat    300
tttctctgtc ttctcatctt ttcgtccatc actgaaccat ctcctctctc tgccaagtta    360
gaggaggcgg gaaaaaacct ccaaataact ctcttttctc cctcccctcc cctcgcctcc    420
ttttcctcgc ctccagtcca gtcttctggt ttcagacggc cccttttaatt taagttccct   480
agtttcccct gggagatctg gccaagaact acccggtcgg ggcggaacga catccggtaa    540
cgcccctcac agttcacttc cgtcctccac ctgcgtctct gcttgcgcca tttcctccag    600
cctggagtgt ctccgcccctt cccgcctccc gtct                                634
```

<210> SEQ ID NO 5
<211> LENGTH: 1250
<212> TYPE: DNA
<213> ORGANISM: Homo sapiens

<400> SEQUENCE: 5

```
tgagatatgt tgctttgctt cgcttctgtc aataagatga gaataacggt acctactcct      60
tagtattaaa tgattaagta tgttaacagg gagagggcca aacgtttgtt gttttattac     120
acagcaggac atcaggtctt acttttgtag ctccccatct caaagacggg gatagcaaat    180
gtttcattca ggaaaaaaat ccaggttgaa caatggggct gttggggcgg ggccaagaac    240
attctgctcg aattaacagt attaatgggc cgggcgcggt ggctcacgcc tgtaatccca    300
gcactctggg aggccgaagt gggtggatca cctgaggtca tacatgggtg aagccccgtc    360
```

```
tctactaaaa aaacaaaaat tgctgggcg tggtggcggg cgcctgtaat cctagctact      420
cgggaggctg aggcaggaga atcgcttgaa cccgggaagc agcggttgca gtgagccgag      480
atcaggacat tgcactcccg cctgggcgac agggcgagac tctgtctcaa aacaaaaaca      540
aaaacagtat taatggaatg tagtataacc ctcaagccct actattaaca cttgggccg       600 aatccagacc ccgtcttccc gctcggattc agaaccctt cctgactcac tggccctagg       660
gcatcagcta cctcggacag catccttttg ggaaaatacc gcccaccagc ccacgactg       720 ggaaagagtc gggaaacacc cccgagcaat ccagttccct gagacttccc tcctccctcc      780
cctcagctag ggcctgccgg ttcctagtgc gtgcccagca gtcctcaggt caccttcact      840
accgggccaa ggaccccgtg ggaactcgca gccttcgcca cactcgttcc tcgcgcatcc      900
atggaggggt gcctacagag aagacctgcg tggcaaaaac ctaaacgaag agatgagggg      960
catggagagg agtaggataa agaataaag ataacagtgg ggggagacg ttagtttcct       1020 ttatatcttt tgttactggc ggtagcagtg aagttagaaa cggttttaaa acaaatttca      1080
gacaggcatt ttccaaaggc aagcctggag cgcacggatc tgtataaccg cggaaggccc      1140
tgtttccggt cccttgcgcc tgcgctcttg cagccaagaa ggcgggaggc tggagtagag      1200
ggaagcctgc aaccggaagt gaaggcagat ttccctcctt cgtcgctgtt              1250
```

<210> SEQ ID NO 6
<211> LENGTH: 1386
<212> TYPE: DNA
<213> ORGANISM: Homo sapiens

<400> SEQUENCE: 6

```
gccccatctc cttgggctgc ccgtgcttcg tgctttggac taccgcccag cagtgtcctg       60
ccctctgcct gggcctcggt ccctcctgca cctgctgcct ggatcccgg cctgcctggg      120 cctgggcctt ggttctcccc atgacaccac ctgaacgtct cttcctccca agggtgtgtg      180
gcaccaccct acacctcctc cttctggggc tgctgctggt tctgctgcct ggggcccagg      240
ggctccctgg tgttggcctc acaccttcag ctgcccagac tgcccgtcag caccccaaga      300
tgcatcttgc ccacagcacc ctcaaacctg ctgctcacct cattggagac cccagcaagc      360
agaactcact gctctggaga gcaaacacgg accgtgcctt cctccaggat ggtttctcct      420
tgagcaacaa ttctctcctg gtccccacca gtggcatcta cttcgtctac tcccaggtgg      480
tcttctctgg gaaagcctac tctcccaagg ccacctcctc cccactctac ctggcccatg      540
aggtccagct cttctcctcc cagtacccct tccatgtgcc tctcctcagc tcccagaaga      600
tggtgtatcc agggctgcag gaaccctggc tgcactcgat gtaccacggg gctgcgttcc      660
agctcaccca gggagaccag ctatccaccc acacagatgg catcccccac ctagtcctca      720
gccctagtac tgtcttcttt ggagccttcg ctctgtagaa cttggaaaaa tccagaagaa      780
aaaaataatt gatttcaaga ccttctcccc attctgcctc cattctgacc atttcagggg      840
tcgtcaccac ctctcctttg gccattccaa cagctcaagt cttccctgat caagtcaccg      900
gagctttcaa agaaggaatt ctaggcatcc caggggacca cacctccctg aaccatccct      960
gatgtctgtc tggctgagga tttcaagcct gcctaggaat tcccagccca agctgttgg      1020 tctgtcccac cagctaggtg gggcctagat ccacacacag aggaagagca ggcacatgga     1080
ggagcttggg ggatgactag aggcagggag gggactattt atgaaggcaa aaaaattaaa     1140
ttatttattt atggaggatg gagagagggg aataatagaa gaacatccaa ggagaaacag     1200
agacaggccc aagagatgaa gagtgagagg gcatgcgcac aaggctgacc aagagagaaa     1260
```

| | |
|---|---|
| gaagtaggca tgagggatca cagggcccca gaaggcaggg aaaggctctg aaagccagct | 1320 |
| gccgaccaga gccccacacg gaggcatctg caccctcgat gaagcccaat aaacctcttt | 1380 |
| tctctg | 1386 |

<210> SEQ ID NO 7
<211> LENGTH: 1459
<212> TYPE: DNA
<213> ORGANISM: Homo sapiens

<400> SEQUENCE: 7

| | |
|---|---|
| ccgagcttct taaacacagg ccttgggcta cggctctggg ggtacttggg ggggcggggg | 60 |
| caggtctgat gagtaacccc tcccccagg ttccagagga agaagcctcc acatctgtct | 120 |
| gccggcccaa gagttccatg gcctccactt cccgccgcca acgccgagaa cgtcgctttc | 180 |
| gtcgttactt gtctgcagga cggctggtcc gggcccaggc cctcctccag cgacacccag | 240 |
| gcctcgatgt agatgctggg cagccccac cactgcaccg gcctgtgcc cgccacgatg | 300 |
| cccctgccct gtgcctgctg cttcggctcg gggctgaccc tgcccaccag gaccgccatg | 360 |
| gggacacggc actgcatgct gctgcccgcc agggcccaga tgcctacacc gatttcttcc | 420 |
| tcccgctgct aagccgctgt ccctctgcca tgggaataaa gaataaggat ggggagaccc | 480 |
| ctggccaaat tttgggctgg gaccccccct gggattctgc tgaagaggag gaagaagatg | 540 |
| atgcctccaa ggagcgggaa tggagacaga agctccaggg tgagctggag gacgagtggc | 600 |
| aggaagtcat ggggaggttt gaaggtgatg cctcccatga aacccaggaa cctgagtcct | 660 |
| tctcagcctg gtcagatcgc ctggcccggg aacatgccca gaagtgccag cagcagcagc | 720 |
| gagaagcaga gggatcctgt cgaccccac gtgctgaggg ctccagccag agctggcgac | 780 |
| acgaggagga ggagcagcgg ctcttcaggg agcgagcccg ggccaaggag gaagagctgc | 840 |
| gtgagagccg agccaggagg cgcaggagg ctctagggga ccgagaaccc aagccaacca | 900 |
| gggccgggcc cagggaagag caccccagag gagcggggag gggcagcctc tggcgatttg | 960 |
| gtgatgtgcc ctggccctgc cctggggag gggacccaga ggccatggct gcagccctgg | 1020 |
| tggccagggg cccccctttg gaggaacagg gggctctgag gaggtacttg agggtccagc | 1080 |
| aggtccgctg gcaccctgac cgcttcctgc agcgattccg aagccagatt gagacctggg | 1140 |
| agctgggccg tgtgatggga gcagtgacag ccctttctca ggccctgaat cgccatgcag | 1200 |
| aggccctcaa gtgaccctag gaagaagca agaaacttcg gggctgcagc ctcaggatga | 1260 |
| ggcagaagga agggtaaggg aaaggatggg gaccacaagg aagagccagg tgctgctcag | 1320 |
| cagaggatat gggtgggagc gaaagttgta acaagtgggg gtgggggtg cgggccgcca | 1380 |
| ccactgctcc ttgactctgc cgtttcctaa taagacctgg ttccacatct caaaaaaaaa | 1440 |
| aaaaaaaaa aaaaaaaa | 1459 |

<210> SEQ ID NO 8
<211> LENGTH: 1854
<212> TYPE: DNA
<213> ORGANISM: Homo sapiens

<400> SEQUENCE: 8

| | |
|---|---|
| acaggcattt tccaaaggca agcctggagc gcacggatct gtataaccgc ggaaggccct | 60 |
| gtttccggtc ccttgcgcct gcgctcttgc agccaagaag gcgggaggct ggagtagagg | 120 |
| gaagcctgca accggaagtg aaggcagatt tccctccttc gtcgctgttg ctgccgccat | 180 |
| acgcgctctc cctgtttagc tcttctgtta gaaatagtat cttttgttttc ctttgctgtt | 240 |

-continued

```
cctcaatccc ctactcttca ccccttgttt tcacctattt tgcgagaacc catccagatc     300 cccottccct tcttccoctg ccggcccagt tatggcagag aacgatgtgg acaatgagct     360
cttggactat gaagatgatg aggtggagac agcagctggg ggagatgggg ctgaggcccc     420
tgccaagaag gatgtcaagg gctcctatgt ctccatccac agctctggct ttcgtgactt     480
cctgctcaag ccagagttgc tccgggccat tgtcgactgt ggctttgagc atccgtcaga     540
agtccagcat gagtgcatcc ctcaggccat tctgggaatg gatgtcctgt gccaggccaa     600
gtcgggcatg ggaaagacag cagtgtttgt cttggccaca ctgcaacagc tggagccagt     660
tactgggcag gtgtctgtgc tggtgatgtg tcacactcgg gagttggctt ttcagatcag     720
caaggaatat gagcgcttct ctaaatacat gcccaatgtc aaggttgctg ttttttttgg     780
tggtctgtct atcaagaagg atgaagaggt gctgaagaag aactgcccgc atatcgtcgt     840
ggggactcca ggccgtatcc tagccctggc tcgaaataag agcctcaacc tcaaacacat     900
taaacacttt attttggatg aatgtgataa gatgcttgaa cagctcgaca tgcgtcggga     960
tgtccaggaa attttttcgca tgaccccccca cgagaagcag gtcatgatgt tcagtgctac    1020
cttgagcaaa gagatccgtc cagtctgccg caagttcatg caagatccaa tggagatctt    1080
cgtggatgat gagacgaagt tgacgctgca tgggttgcag cagtactacg tgaaactgaa    1140
ggacaacgag aagaaccgga agctctttga ccttctggat gtccttgagt caaccaggt     1200 ggtgatcttt gtgaagtctg tgcagcggtg cattgccttg cccagctac tagtggagca     1260 gaacttccca gccattgcca tccaccgtgg gatgccccag gaggagaggc tttctcggta    1320
tcagcagttt aaagattttc aacgacgaat tcttgtggct accaacctat ttggccgagg    1380
catggacatc gagcgggtga acattgcttt taattatgac atgcctgagg attctgacac    1440
ctacctgcat cgggtggcca gagcaggccg gtttggcacc aagggcttgg ctatcacatt    1500
tgtgtccgat gagaatgatg ccaagatcct caatgatgtg caggatcgct ttgaggtcaa    1560
tattagtgag ctgcctgatg agatagacat ctcctcctac attgaacaga cacggtagaa    1620
gactcgccca ttttggaatg tgaccgtctg tccttcagga gaggacacca gggtgggggt    1680
gaaggagaca ctactgcccc cacccctgac agcccccacc ccatggcttc catcttttgc    1740
atcaccacca ctcctgaacc cccattctg attgtcaga attttttttt aacaaaacta      1800
aaaatgaaac acatgtgtct gtggtatcta aaaaaaaaaa aaaaaaaaaa aaaa          1854
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9

```
actcagccaa gggtgcagag                                                   20
```

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10

```
cttcctcagg gattgagacc tc                                                22
```

<210> SEQ ID NO 11
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
tccaaagcac gaagcacggg cagcccaagg agatggggca ggagagcctc acctgctgtg    60
cggagcccct gggcccggac gctcaggtcc ctttatagag gaagcggcag tggcagcgtg   120
g                                                                   121

<210> SEQ ID NO 12
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
tccaaagcac gaagcacggg cagcccaagg agatggggca ggagagcctc acctgctgtg    60
tggagcccct gggcccggac gctcaggtcc ctttatagag gaagcggcag tggcagcgtg   120
g                                                                   121

<210> SEQ ID NO 13
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
agagaaaccc caaggtgagc agagggagac agagagagac aggaagggaa cagagaggaa    60
tcatggcaga aacagagaat gtgtgacaga gacaatgaga ctgacagatg gagagtcaga   120
g                                                                   121

<210> SEQ ID NO 14
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
agagaaaccc caaggtgagc agagggagac agagagagac aggaagggaa cagagaggaa    60
ccatggcaga aacagagaat gtgtgacaga gacaatgaga ctgacagatg gagagtcaga   120
g                                                                   121

<210> SEQ ID NO 15
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 15
tcacaccttc agctgcccag actgcccgtc agcaccccaa gatgcatctt gcccacagca    60
ccctcaaacc tgctgctcac ctcattggta aacatccacc tgacctccca gacatgtccc    120
c    121

<210> SEQ ID NO 16
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
tcacaccttc agctgcccag actgcccgtc agcaccccaa gatgcatctt gcccacagca    60
acctcaaacc tgctgctcac ctcattggta aacatccacc tgacctccca gacatgtccc    120
c    121

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tttaaggctc aggagcccag    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tccctgttgt tgtcccactg    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atatcatgta cccggcagac    20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tggtctcaca tcactgttac gc    22

```
<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tcttcccgct cggattcag                                                    19

<210> SEQ ID NO 22
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
aagcttacct aaacagggag agcgcgtatg gcggcagcaa cagcgacgaa ggagggaaat       60
gtgccttcac ttccggttgc aggcttccct ctactccagc ctcccgcctt cttggctgca     120
a                                                                      121

<210> SEQ ID NO 23
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
aagcttacct aaacagggag agcgcgtatg gcggcagcaa cagcgacgaa ggagggaaat       60
ctgccttcac ttccggttgc aggcttccct ctactccagc ctcccgcctt cttggctgca     120
a                                                                      121
```